US012758609B2

(12) United States Patent
Middleton et al.

(10) Patent No.: US 12,758,609 B2
(45) Date of Patent: Oct. 13, 2026

(54) LEUPROLIDE ACETATE COMPOSITIONS AND METHODS OF USING THE SAME TO TREAT BREAST CANCER

(71) Applicant: Tolmar International Limited, Dublin (IE)

(72) Inventors: John Middleton, Fort Collins, CO (US); Avinash Nangia, Fort Collins, CO (US); John Arthur McLane, Loveland, CO (US); Terri L. Morton, Loveland, CO (US)

(73) Assignee: Tolmar International Limited, Dublin (IE)

( * ) Notice: Subject to any disclaimer, the term of this patent is extended or adjusted under 35 U.S.C. 154(b) by 0 days.

(21) Appl. No.: 19/345,133

(22) Filed: Sep. 30, 2025

(65) Prior Publication Data

US 2026/0027176 A1 Jan. 29, 2026

Related U.S. Application Data

(62) Division of application No. 17/614,312, filed as application No. PCT/IB2020/054984 on May 26, 2020, now Pat. No. 12,453,754.

(60) Provisional application No. 62/853,153, filed on May 27, 2019.

(51) Int. Cl.

| | |
|---|---|
| ***A61K 9/00*** | (2006.01) |
| ***A61K 31/138*** | (2006.01) |
| ***A61K 31/4196*** | (2006.01) |
| ***A61K 31/566*** | (2006.01) |
| ***A61K 38/09*** | (2006.01) |
| ***A61K 47/22*** | (2006.01) |
| ***A61K 47/34*** | (2017.01) |
| ***A61P 35/00*** | (2006.01) |

(52) U.S. Cl.

CPC ............ *A61K 38/09* (2013.01); *A61K 9/0024* (2013.01); *A61K 31/138* (2013.01); *A61K 31/4196* (2013.01); *A61K 31/566* (2013.01); *A61K 47/22* (2013.01); *A61K 47/34* (2013.01); *A61P 35/00* (2018.01)

(58) Field of Classification Search

CPC .... A61K 38/09; A61K 9/0024; A61K 31/138; A61K 31/4196; A61K 31/566; A61K 47/22; A61K 47/34; A61K 45/06; A61K 2300/00; A61K 47/12; A61P 35/00; A61P 15/00

See application file for complete search history.

(56) References Cited

U.S. PATENT DOCUMENTS

| | | | | |
|---|---|---|---|---|
| 4,938,763 | A | 7/1990 | Dunn et al. | |
| 5,324,519 | A | 6/1994 | Dunn et al. | |
| 5,702,716 | A | 12/1997 | Dunn et al. | |
| 5,744,153 | A | 4/1998 | Yewey et al. | |
| 5,990,194 | A | 11/1999 | Dunn et al. | |
| 8,840,916 | B2 | 9/2014 | Dunn | |
| 9,254,307 | B2 | 2/2016 | Dunn et al. | |
| 9,539,333 | B2 | 1/2017 | Dunn | |
| 9,914,802 | B2 | 3/2018 | Dunn | |
| 2014/0357574 | A1* | 12/2014 | Dunn | A61K 38/09 604/82 |
| 2016/0033180 | A1 | 2/2016 | Russo et al. | |
| 2016/0106805 | A1 | 4/2016 | Dunn et al. | |
| 2016/0106847 | A1 | 4/2016 | Dadey et al. | |
| 2020/0390849 | A1 | 12/2020 | Li et al. | |
| 2022/0026576 | A1 | 1/2022 | Baribault et al. | |
| 2022/0331523 | A1 | 10/2022 | Sherman et al. | |
| 2023/0057569 | A1 | 2/2023 | Jadhav et al. | |

FOREIGN PATENT DOCUMENTS

| | | | | |
|---|---|---|---|---|
| DE | 202009010095 U1 | 10/2009 | | |
| EP | 3975990 A1 | 4/2022 | | |
| KR | 102162217 B1 | 10/2020 | | |
| WO | WO-2017024027 A1 * | 2/2017 | | A61K 38/09 |
| WO | 2020240417 A1 | 3/2020 | | |
| WO | 2023126463 A1 | 7/2023 | | |

OTHER PUBLICATIONS

Bellet et al. "Twelve-Month Estrogen Levels in Premenopausal Women With Hormone Receptor-Positive Breast Cancer Receiving Adjuvant Triptorelin Plus Exemestane or Tamoxifen in the Suppression of Ovarian Function Trail (SOFT): The SOFT-EST Substudy," Journal of Clinical Oncology, vol. 34, No. 14 (May 10, 2016), 25 pages.

Boughey, et al. "Abstract GS4-01: Impact of Breast Conservation Therapy on Local Recurrance in Patients with Multiple Ipsilateral Breast Cancer—Results from ACOSOG Z11102(Alliance)," General Session Abstracts (Mar. 1, 2023), https://aacrjournals.org/cancerres/article/83/5_Supplement/GS4-01/71748/Abstract-GS4-01-Impact-of-Breast-Concervation (2 pages).

Clowse, et al. "Ovarian Preservation by GnRH Agonists during Chemotherapy: a Meta_Analysis," Journal of Women's Health, vol. 18, No. 3 (2009), pp. 311-319.

Lambertini , et al. "Conadotropin-Releasing Hormone Agonists During Chemotherapy for Preservation of Ovarian Function and Fertility in Premenopausal Patients With Early Breast Cancer: a Systematic Review and Meta-Analysis of Individual Patient-Level Data," Journal of Clinical Onocology, vol. 36, No. 19 (Jul. 1, 2018), pp. 1981-1990 (12 pages).

Lambertini et al. "Ovarian suppression using luteinizing hormone-releasing agonists during chemotherapy to preserve ovarian function and fertility of breast cancer patients: a meta-analysis of randomized studies," Annals of Oncology 26: 2408-2419 (2015) (Year:2015).

(Continued)

*Primary Examiner* — Julie Ha
*Assistant Examiner* — Kristina M Hellman
(74) *Attorney, Agent, or Firm* — Ballard Spahr LLP

(57) ABSTRACT

Compositions and methods for suppressing ovarian function in subjects with hormone receptor-positive breast cancer.

24 Claims, 4 Drawing Sheets

(56) References Cited

OTHER PUBLICATIONS

Lauretta, et al. "Gender in Endocrine Diseases: Role of Sex Gonadal Hormones," International Journal of Endocrinology, vol. 2018, Published Oct. 21, 2018 (11 pages).
Leuproelin acetate from the preservation of ovarian function in premenopausal women with neoplastic disease undergoing chemotherapy NIHR Innovation Observatory Evidence Briefing (Jul. 2018), NIHRO (HSRIC) ID: 24223 (9 pages).
Lupron Depot prescribing information (Jun. 2014).
Kurebayashi et al., "Efficacy and safety of leuprorelin acetate 6-month depot, TAP-144-SR (6M), in combination with tamoxifen in postoperative, premenopausal patients with hormone receptor-positive breast cancer: a phase III, randomized, open-label, parallel-group comparative study," Breast Cancer, vol. 24, Mar. 26, 2016, pp. 161-170.
Nelson, et al. "Estrogen production and action," American Academy of Dermatology, vol. 45, No. 3 (9 pages).
Ravivarapu et al. "Sustained Activity and Release of Leuprolide Acetate from an In Situ Forming Polymeric Implant," AAPS PharmSciTech, 2000, vol. 1, No. 1, article 1, 8 pages.
Ravivarapu et al. "Sustained Suppression of Pituitary-Gonadal Axis with an Injectable, In Situ Forming Implant of Leuprolide Acetate," Journal of Pharmaceutical Sciences, Jun. 2000, vol. 89, No. 6, pp. 732-741.
Sartor et al. "An Eight-Month Clinical Study of LA-2575 30.0 mg: a New 4-Month, Subcutaneous Delivery System for Leuprolide Acetate in the Treatment of Prostate Cancer," Adult Urology 62 (2), 2003, 5 pages.
Song et al. "Effect of leuprolide acetate on ovarian function after cyclophosphamide-doxorubicin-based chemotherapy in premenopausal patients with breast cancer: results from a phase II randomized trial," Med. Oncol (2013) 30:667, published Aug. 1, 2013 (8 pages).
Schmid et al., "Leuprorelin Acetate Every-3-Months Depot Versus Cyclophosphamide, Methotrexate, and Fluorouracil as Adjuvant Treatment in Premenopausal Patients With Node-Positive Breast Cancer: The TABLE Study," Journal of Clinical Oncology, vol. 25, No. 18, Jun. 20, 2007, pp. 2509-2515.
Tesch et al. "Estrongen levels in young women with hormone receptor-positive breast cancer on ovarian function supression therapy," NPJ Breast Cancer (2024) 10:67 (8 pages).

* cited by examiner

LEUPROLIDE ACETATE COMPOSITIONS AND METHODS OF USING THE SAME TO TREAT BREAST CANCER

CROSS-REFERENCE TO RELATED APPLICATIONS

This is a divisional application of U.S. application Ser. No. 17/614,312, filed Nov. 24, 2021, which is a national stage application of PCT Application No. PCT/IB2020/054984, filed May 26, 2020, which claims priority to U.S. Provisional Application No. 62/853,153, filed May 27, 2019, the contents of each of which are incorporated into this application by reference.

TECHNICAL FIELD

This invention relates generally to the field of oncology. Described herein are leuprolide compositions that are particularly useful in suppression of ovarian function and in methods of treating hormone receptor-positive breast cancer.

BACKGROUND

Breast cancer is the most common form of cancer and the leading cause of cancer death in women worldwide. Approximately 80% of all breast cancers express and are dependent on the estrogen receptor (ER) for tumor growth and progression. Modulation of hormone activity and/or synthesis, particularly that of estrogens, is the mainstay of therapeutic approaches in women with hormone receptor-positive (HR-positive) breast cancer. Ovarian suppression is an important element of therapy in pre/perimenopausal patients with medium or high-risk, HR-positive, human epidermal growth factor receptor 2 (HER2)-negative disease receiving endocrine therapy (including aromatase inhibitors [AIs]), to further reduce estrogen levels.

In clinical practice consistent with American Society of Clinical Oncology and National Comprehensive Cancer Network® guidelines, gonadotropin-releasing hormone (GnRH) agonists are used in the United States (US) to suppress ovarian function in pre/perimenopausal patients with breast cancer with a moderate-to higher-risk for recurrence. GnRH agonists are not administered as a monotherapy in the treatment of patients with HR-positive breast cancer. Current treatment strategies involve the use of adjuvant endocrine therapies such as selective estrogen receptor modulators (SERMs), selective estrogen receptor degraders (SERDs), and other drugs that decrease the release of endogenous non-ovarian estrogen (such as aromatase inhibitors [AIs]).

There is a need for a drug formulation that effectively and consistently achieves ovarian function suppression in HR-positive breast cancer patients over an extended period of time to be used concurrently with these adjuvant endocrine therapies and other breast cancer therapies.

SUMMARY

The invention concerns methods for suppressing ovarian function and methods of treating hormone receptor-positive (HR-positive) breast cancer in a breast cancer patient by administration of an extended release, biodegradable polymer composition comprising leuprolide or a pharmaceutically acceptable salt or analog thereof.

Thus, in one aspect, this disclosure provides methods of suppressing ovarian function in subjects with HR-positive breast cancer by administering a therapeutically effective amount of a flowable, extended release composition comprising an organic solvent, leuprolide or a pharmaceutically acceptable salt or analog thereof, and a biodegradable polymer to the HR-positive breast cancer patient in need of such treatment. Upon injection of the flowable, extended release composition into the subject and contact with bodily fluid, the organic solvent in the flowable, extended release composition dissipates and an in situ solid or semi-solid depot forms.

In these methods, the biodegradable polymer may be a poly (lactide-co-glycolide) (PLG) copolymer comprising a lactide to glycolide monomer molar ratio ranging from about 70:30 to about 80:20, inclusive, or in one aspect, up to about 85:15 inclusive, wherein the polymer has substantially no titratable carboxylic acid groups and wherein at least one distal end group of the polymer is hydroxyl-terminated. In these methods, the biodegradable polymer may preferably be a poly(lactide-co-glycolide) copolymer comprising a lactide to glycolide monomer molar ratio of 75:25, wherein the polymer has substantially no titratable carboxylic acid groups and wherein at least one distal end group of the polymer is hydroxyl-terminated. In these methods, the biodegradable polymer may have a weight average molecular weight from about 15 kDa to about 45 kDa, or from about 15 kDa to about 26 kDa, or from about 17 kDa to about 21 kDa. In these methods, the biodegradable polymer may be present in an amount from about 35 wt. % to about 60 wt. % of the flowable, extended release composition.

In these methods, the organic solvent may be selected from N-methyl-2-pyrrolidone (NMP), acetone, cyrene, butyrolactone, ε-caprolactone, caprolactam, N-cycylohexyl-2-pyrrolidone, diethylene glycol monomethyl ether, dimethylacetamide, N,N-dimethyl formamide, dimethyl sulfoxide (DMSO), ethyl acetate, ethyl lactate, N-ethyl-2-pyrrolidone, glycerol formal, glycofurol, N-hydroxyethyl-2-pyrrolidone, isopropylidene glycerol, lactic acid, methoxypolyethylene glycol, methoxypropyleneglycol, methyl acetate, methyl ethyl ketone, methyl lactate, benzyl benzoate (BnBzO), polysorbate 80, polysorbate 60, polysorbate 40, polysorbate 20, polyoxyl 35, polyethylene glycol (PEG), hydrogenated castor oil, polyoxyl 40hydrogenated castor oil, sorbitan monolaurate, sorbitan monostearate, sorbitan monooleate, benzyl alcohol, n-propanol, isopropanol, tert-butanol, propylene carbonate, propylene glycol, 2-pyrrolidone, α-tocopherol, triacetin, tributyl citrate, acetyl tributyl citrate, acetyl triethyl citrate, triethyl citrate, esters thereof, and combinations thereof. In these methods, the organic solvent is preferably N-methyl-2-pyrrolidone.

In these methods, the pharmaceutically acceptable salt or analog of leuprolide may selected be from the group consisting of leuprolide acetate, leuprolide monoacetate, leuprolide oleate, leuprolide palmitate, leuprolide mesylate, leuprolide trifluoracetic acid (TFA), leuprolide trifluoroacetate, leuprolide (5-9), (D-His2)-leuprolide trifluoracetic acid (TFA), leuprolide hydrochloric acid (HCL), leuprolide-D5 acetate, leuprolide (L-Leu), and combinations thereof. In these methods, the pharmaceutically acceptable salt of leuprolide is preferably leuprolide acetate. In these methods, the composition may contain about 26 mg to about 30 mg of a leuprolide free base equivalent, for example, the flowable extended release composition may contain about 28 mg to about 32 mg of leuprolide acetate. In these methods, the composition may preferably contain about 28 mg of a leuprolide free base equivalent, for example, the flowable, extended release composition may contain about 30 mg of leuprolide acetate.

In these methods, the HR-positive breast cancer may be estrogen receptor (ER) and/or progesterone receptor (PgR) positive breast cancer. In these methods, the breast cancer may be HR-positive, human epidermal growth factor receptor 2 (HER2)-negative breast cancer.

In these methods, the subject may be a premenopausal or a perimenopausal woman. In these methods, the subject may be at least 18 years of age. In these methods, the subject may be at least 18 years of age and less than 40 years of age, or at least 18 years of age and less than 45 years of age, or at least 18 years of age and less than 55 years of age.

In these methods, the flowable extended release composition may be administered concurrently with one or more therapeutic treatments for HR-positive breast cancer, including, but not limited to an endocrine therapy. In these methods, the flowable, extended release composition may be administered concurrently with an anti-hormonal agent and/or an aromatase inhibitor. In these methods, the flowable extended release composition may be administered concurrently with one or more of tamoxifen, letrozole, anastrozole, and exemestane. Alternatively or additionally, the flowable, extended release composition may be administered concurrently with chemotherapy and/or radiotherapy.

In these methods, the flowable extended release composition may be administered to the subject subcutaneously. In these methods, the flowable, extended release composition may be administered to the subject about once every 90 days (i.e., about once every 3 months). In these methods, the flowable, extended release composition may be administered to the subject at least twice, at least 3 times, at least 4 times, at least 8 times, at least 12 times, at least 16 times, at least 20 times, or more than 20 times.

In these methods, the administration of the flowable extended release composition may result in the in vivo release of about 10 mg of leuprolide acetate per month from the in situ solid or semi-solid depot formulation into the subject. In these methods, the administration of the flowable, extended release composition may result in approximately linear release of leuprolide or a pharmaceutically acceptable salt or analog thereof (e.g., leuprolide acetate) over about 90 days (i.e., about 3 months) after post-dose plasma concentration burst from the composition into the subject.

In these methods, the administration of the flowable, extended release composition may result in an Area Under the Curve (AUC) of leuprolide acetate in the subject between about 10 day·ng/mL and about 225 day·ng/mL. In these methods, the administration of the flowable, extended release composition may result in a mean Area Under the Curve (AUC) of leuprolide acetate over about 80 days in the subject between about 75 day·ng/mL and about 100 day·ng/mL. In these methods, the administration of the flowable, extended release composition results in an initial burst release of leuprolide acetate from the composition into the subject, and the administration of the flowable, extended release composition may result in an Area Under the Curve (AUC) of leuprolide acetate in the subject between about 90 day·ng/mL and about 370 day·ng/mL, or a mean Area Under the Curve (AUC) of leuprolide acetate over about 80 days in the subject between about 205 day·ng/mL and about 210 day·ng/mL.

In these methods, the administration of the flowable, extended release composition, alone or concurrently with one or more a therapeutic treatments for HR-positive breast cancer, including but not limited to an endocrine therapy, such as an anti-hormonal agent and an aromatase inhibitor, may reduce the subject's estradiol (E2) production to post-menopausal levels (<20 pg/mL). In these methods, the administration of the flowable, extended release composition, alone or concurrently with one or more of an anti-hormonal agent and/or an aromatase inhibitor, may reduce the subject's estradiol to about 20 pg/mL or less, or to about 10pg/mL or less. In these methods, the administration of the flowable, extended release composition concurrently with an aromatase inhibitor, may reduce the subject's estradiol to about 2.7 pg/mL or less. In these methods, the administration of the flowable, extended release composition, alone or concurrently with one or more of an anti-hormonal agent and/or an aromatase inhibitor, may reduce the subject's follicle stimulating hormone (FSH) level to about 40 IU/L or less.

In another aspect, this disclosure provides an article of manufacture that includes a first container containing leuprolide or a pharmaceutically acceptable salt or analog thereof, and a second container containing a biodegradable polymer and an organic solvent. These articles may include instructions for the use thereof, and may also include instructions for combining the contents of the first and second containers to form a flowable, extended release composition for administration to a subject. In these articles, the first container may contain about 26 mg to about 30 mg of a leuprolide free base equivalent, for example, the first container may contain about 28 mg to about 32 mg of leuprolide acetate. In these articles, the first container may preferably contain about 28 mg of a leuprolide free base equivalent, for example, about 30 mg of leuprolide acetate. In these articles, the second container may contain less than 1.0 mL of a biodegradable polymer/organic solvent composition, more preferably the second container may contain from about 0.30 mL and about 0.50 mL of a biodegradable polymer/organic solvent composition, or preferably about 0.375 mL of a biodegradable polymer/organic solvent composition.

In these articles, the biodegradable polymer may be a poly(lactide-co-glycolide) copolymer comprising a lactide to glycolide monomer molar ratio ranging from about 70:30 to about 80:20, inclusive, or in one aspect, up to about 85:15 inclusive, wherein the polymer has substantially no titratable carboxylic acid groups and wherein at least one distal end group of the polymer is hydroxyl-terminated. In these articles, the biodegradable polymer may preferably be a poly(lactide-co-glycolide) copolymer comprising a lactide to glycolide monomer molar ratio of 75:25, wherein the polymer has substantially no titratable carboxylic acid groups and wherein at least one distal end group of the polymer is hydroxyl-terminated. In these articles, the biodegradable polymer may have a weight average molecular weight from about 15 kDa to about 45 kDa, or from about 15 kDa to about 26 kDa, or from about 17 kDa to about 21 kDa. In these articles, the biodegradable polymer may comprise from about 35 wt. % to about 60 wt. % of the flowable, extended release composition.

In these articles, the organic solvent may be selected from N-methyl-2-pyrrolidone (NMP), acetone, cyrene, butyrolactone, ε-caprolactone, caprolactam, N-cycylohexyl-2-pyrrolidone, diethylene glycol monomethyl ether, dimethylacetamide, N,N-dimethyl formamide, dimethyl sulfoxide (DMSO), ethyl acetate, ethyl lactate, N-ethyl-2-pyrrolidone, glycerol formal, glycofurol, N-hydroxyethyl-2-pyrrolidone, isopropylidene glycerol, lactic acid, methoxypolyethylene glycol, methoxypropyleneglycol, methyl acetate, methyl ethyl ketone, methyl lactate, benzyl benzoate (BnBzO), polysorbate 80, polysorbate 60, polysorbate 40, polysorbate 20, polyoxyl 35, polyethylene glycol (PEG), hydrogenated castor oil, polyoxyl 40 hydrogenated castor oil, sorbitan monolaurate, sorbitan monostearate, sorbitan monooleate, benzyl alcohol, n-propanol, isopropanol, tert-butanol, propylene carbonate, propylene glycol, 2-pyrrolidone, α-tocopherol, triacetin, tributyl citrate, acetyl tributyl citrate, acetyl triethyl citrate, triethyl citrate, esters thereof, and combinations thereof. In these articles, the organic solvent is preferably N-methyl-2-pyrrolidone.

In these articles, the first and second containers may be first and second chambers of a dual chamber syringe, and the contents of the first and second chambers may be mixed by adding the contents of the second chamber to the first chamber, or vice versa, and mixing the contents to form the flowable, extended release composition. In these articles, the first and second containers may be first and second syringes and the contents of the first and second syringes may be mixed by coupling the syringes together and transferring the contents back and forth between the two syringes until the contents are effectively mixed together to form the flowable, extended release composition. In these articles, the injection volume of the flowable, extended release composition may be less than about 1.0 mL, preferably less than about 0.5 mL, or more preferably about 0.375 mL.

These articles may also contain a needle adapted to be inserted onto a syringe containing the flowable, extended release composition for subcutaneous administration of the composition to a subject. These articles may also contain a package insert, wherein the package insert provides efficacy and/or safety data for the use of the flowable, extended release composition in the suppression of ovarian function in subjects with HR-positive breast cancer.

Preferred embodiments of this disclosure include an extended release composition for the suppression of ovarian function in a subject with HR-positive breast cancer, comprising about 0.375 mL of a composition comprising N-methyl-2-pyrrolidone, 30 mg of leuprolide acetate, and a biodegradable polymer comprising 75:25 poly (lactide-co-glycolide) (PLG) copolymer segments, wherein the polymer has substantially no titratable carboxylic acid groups and wherein at least one distal end group of the polymer is hydroxyl-terminated. In these extended release compositions, the biodegradable thermoplastic polymer may have the chemical formula: HO—(P)—C(═O)O-Ra-O(O═)C—(P)—OH, wherein Ra is an alkane diradical comprising about 4 to about 8 carbons and is a residue of an alkane diol, and P is a polymeric segment of repeating units of lactide, glycolide, or (lactide-co-glycolide).

This Summary is neither intended nor should it be construed as representative of the full extent and scope of the present invention. Moreover, references made herein to "the present disclosure," or aspects thereof, should be understood to mean certain embodiments of the present invention and should not necessarily be construed as limiting all embodiments to a particular description. The present disclosure is set forth in various levels of detail in this Summary as well as in the attached drawings and the Detailed Description and no limitation as to the scope of the present disclosure is intended by either the inclusion or non-inclusion of elements, components, etc. in this Summary. Additional aspects of the present invention will become more readily apparent from the Detailed Description, particularly when taken together with the figures.

DETAILED DESCRIPTION

Figure 1:
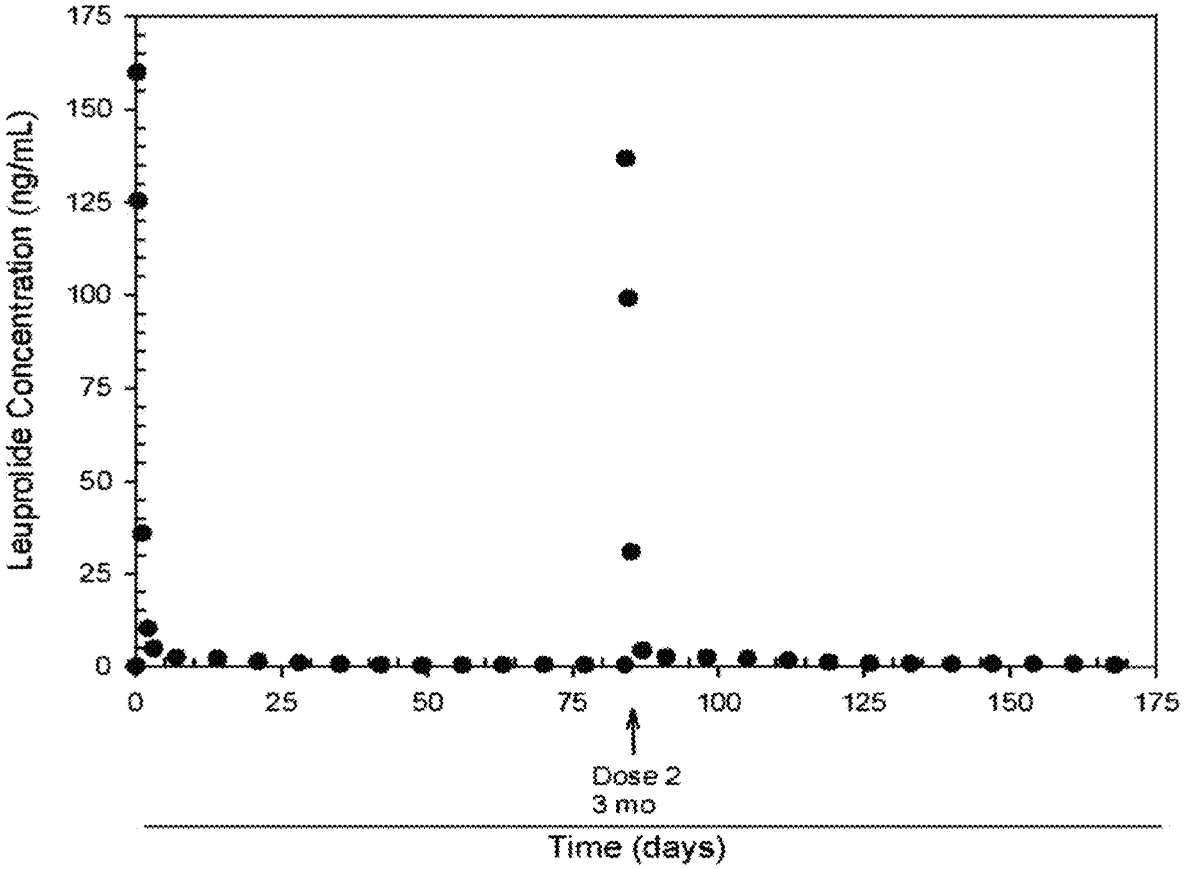
FIG. 1 shows linear serum leuprolide concentration-time profiles simulated for administration of 30 mg of leuprolide acetate injection every 3 months for 2 doses.

Glossary of some abbreviations used herein: area under the concentration-time curve (AUC), confidence interval (CI), maximum concentration (Cmax), complete response (CR), dose limiting toxicity (DLT), gel permeation chromatography (GPC), mitomycin, cisplatin, and 5-fluorouracil (MCF), estrogen receptor (ER), human epidermal growth factor receptor 2 (HER2), hormone receptor (HR), cyclophosphamide, methotrexate, estradiol (E2), estrone (E1), estrone sulfate (E1S), follicle-stimulating hormone (FSH), and luteinizing hormone (LH), luteinizing hormone-releasing hormone (LHRH), metastatic breast cancer (MBC), not significant (NS), overall survival (OS), progressive disease (PD), progression free survival (PFS), pharmacokinetic (PK), partial response (PR), progesterone receptor (PgR), serious adverse event (SAE), and time to maximum plasma concentration ($t_{max}$).

Definitions

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, cicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$) alkyl can be methyl, ethyl, propyl, isopropyl, butyl, iso-butyl, sec-butyl, pentyl, 3-pentyl, or hexyl; ($C_3$-$C_6$) cycloalkyl can be cyclopropyl, cyclobutyl, cyclopentyl, or cyclohexyl; ($C_3$-$C_6$)cycloalkyl ($C_1$-$C_6$) alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; ($C_1$-$C_6$) alkoxy can be methoxy, ethoxy, propoxy, isopropoxy, butoxy, iso-butoxy, sec-butoxy, pentoxy, 3-pentoxy, or hexyloxy; ($C_2$-$C_6$)alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; (C2-C6) alkynyl can be cthynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; ($C_1$-$C_6$)alkanoyl can be acetyl, propanoyl or butanoyl; halo ($C_1$-$C_6$)alkyl can be iodomethyl, bromomethyl, chloromethyl, fluoromethyl, trifluoromethyl, 2-chlorocthyl, 2-fluorocthyl, 2,2,2-trifluoroethyl, or pentafluoroethyl; hydroxy $(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$ alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy.

The terms "molecular weight" and "average molecular weight," unless otherwise specified, mean a weight-average molecular weight as measured by a conventional gel permeation chromatography (GPC) instrument (such as an Agilent 1260 Infinity Quaternary LC with Agilent G1362A Refractive Index Detector) utilizing polystyrene standards and tetrahydrofuran (THF) as the solvent.

The term "chemotherapy" as used herein refers to treatment comprising the administration of a chemotherapy, as defined herein below.

As used herein, the term "endocrine therapy" or "hormone therapy" for breast cancer refers to treatment(s) that block the attachment of estrogen and/or progesterone to receptors in breast cancer cells. Exemplary endocrine therapy agents include selective estrogen receptor modulators (SERMs), selective estrogen receptor degraders (SERDs), aromatase inhibitors (AIs), and may include agents or treatments that effect ovarian suppression.

"Survival" refers to the patient remaining alive and includes overall survival as well as progression free survival.

"Overall survival" or "OS" refers to the patient remaining alive for a defined period of time, such as 1 year, 5 years, etc. from the time of diagnosis or treatment. For the purposes of clinical breast cancer treatment trials, overall survival (OS) is defined as the time from the date of randomization of patient population to the date of death from any cause.

"Progression-free-survival" or "PFS" refers to the patient remaining alive, without the breast cancer progressing or getting worse. For the purpose of clinical breast cancer treatment trials, progression free survival (PFS) is defined as the time from randomization of study population to the first documented progressive disease, or unmanageable toxicity, or death from any cause, whichever occurs first. Disease progression can be documented by any clinically accepted methods, such as, radiographical progressive disease.

By "extending survival" is meant increasing overall or progression free survival in a breast cancer patient, for example a patient treated in accordance with the present invention relative to an untreated patient and/or relative to a patient treated with one or more approved anti-tumor agents, but not receiving treatment in accordance with the present invention.

An "objective response" refers to a measurable response, including complete response (CR) or partial response (PR).

By "complete response" or "CR" is intended the disappearance of all signs of cancer in response to treatment. This does not always mean the cancer has been cured.

"Partial response" or "PR" refers to a decrease in the size of one or more tumors or lesions, or in the extent of cancer in the body, in response to treatment.

The terms "cancer" and "cancerous" refer to or describe the physiological condition in mammals that is typically characterized by unregulated cell growth.

An "advanced" breast cancer is one which has spread outside the breast, either by local invasion or metastasis. Accordingly, the term "advanced" cancer includes both locally advanced and metastatic disease.

A "refractory" cancer is one which progresses even though an anti-tumor agent, such as a chemotherapy, is being or has been administered to the breast cancer patient. An example of a refractory cancer is one which is platinum refractory.

A "recurrent" cancer is one which has regrown, either at the initial site or at a distant site, after a response to initial therapy, such as surgery.

A "locally recurrent" cancer is one that returns after treatment in the same place as a previously treated cancer.

A "non-resectable" or "unresectable" cancer is not able to be removed (resected) by surgery.

"Early-stage breast cancer" herein refers to breast cancer that has not spread beyond the breast or the axillary lymph nodes. Such cancer is generally treated with neoadjuvant or adjuvant therapy.

"Neoadjuvant therapy" refers to systemic therapy given prior to surgery.

"Adjuvant therapy" refers to systemic therapy given after surgery.

"Metastatic" cancer refers to cancer which has spread from one part of the body (e.g., the breast) to another part of the body.

Herein, a "patient" or "subject" is a human patient. The patient may be a female or a male patient. The patient may be a "cancer patient," i.e., one who is suffering or is at risk of suffering from one or more symptoms of cancer, in particular breast cancer.

A "patient population" refers to a group of cancer patients. Such populations can be used to demonstrate statistically significant efficacy and/or safety of a drug, such as leuprolide.

A "relapsed" patient is one who has signs or symptoms of cancer after remission. Optionally, the patient has relapsed after adjuvant or neoadjuvant therapy.

The term "perimenopause" or "menopausal transition" is understood to mean the period of time around menopause during which a woman's body makes its natural transition toward permanent infertility (menopause). Women may start perimenopause at different ages, and may notice signs of progression toward menopause, such as menstrual irregularity, during their 40's, or even as early as their mid-30's. During perimenopause, estrogen levels may rise and fall unevenly, menstrual cycles may lengthen or shorten, and menstrual cycles may begin in which the ovaries do not release an egg (ovulate).

The term "postmenopausal woman" is understood to include not only a woman of advanced age who has passed through menopause, but also a woman who has been hysterectomiaed or for some other reason has suppressed estrogen production, such as one who has undergone long-term administration of corticosteroids, suffer from Cushions' syndrome or have gonadal dysgenesis.

An "anti-tumor agent" refers to a drug used to treat cancer.

"Treatment" refers to both therapeutic treatment and prophylactic or preventative measures, as well as adjunct (add-on) regimens that are administered concurrently with therapeutic treatment measures to provide an additional clinical benefit to the patient and/or maximize the effectiveness of the therapeutic treatment measures. Those subjects in need of treatment include those already with cancer as well as those in which cancer is to be prevented. Hence, the patient to be treated may have been diagnosed as having cancer or may be predisposed or susceptible to cancer.

The term "effective amount" refers to an amount of a drug or drug composition effective to suppress ovarian function, treat cancer, and/or provide another clinical benefit to the patient, such as enhance or maximize the effectiveness of a therapeutic treatment for cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; suppress ovarian function; suppress estradiol levels; suppress follicle stimulating hormone (FSH) levels; and/or relieve to some extent one or more of the symptoms associated with the cancer. To the extent the drug may prevent growth and/or kill existing cancer cells, it may be cytostatic and/or cytotoxic.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $p^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapy" is use of a chemical compound useful in the treatment of cancer. Examples of chemotherapeutic agents, used in chemotherapy, include alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trictylenephosphoramide, triethiylenethiophosphoramide and trimethylolomelamine; TLK 286 (TELCYTA); acetogenins (especially bullatacin and bullatacinone); delta-9-tetrahydrocannabinol (dronabinol, MARINOL); beta-lapachone; lapachol; colchicines; betulinic acid; a camptothecin (including the synthetic analogue topotecan (HYCAMTIN), CPT-11 (irinotecan, CAMPTOSAR), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); cleutherobin; pancratistatin; a sarcodictyin; spongistatin; nitrogen mustards such as chlorambucil, chlornaphazine, estramustine, ifosfamide, mechlorethamine, mechlorethamine oxide hydrochloride, melphalan, novembichin, phenesterine, prednimustine, trofosfamide, and uracil mustard; nitrosureas such as carmustine, chlorozotocin, fotemustine, lomustine, nimustine, and ranimnustine; bisphosphonates, such as clodronate; antibiotics such as the enediyne antibiotics and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, detorubicin, 6-diazo-5-oxo-L-norleucine, doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurca; lentinan; lonidainine; maytansinoids such as maytansine and ansamitocins; mitoguazone; mitoxantronc; mopidanmol; nitracrine; pentostatin; phenamet; pirarubicin; losoxantrone; 2-ethylhydrazide; procarbazine; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE, FILDESIN); dacarbazine; mannomustine; mitobronitol; mitolactol; pipobroman; gacytosine; arabinoside ("Ara-C"); taxanes; chloranbucil; gemcitabine (GEMZAR); 6-thioguanine; mercaptopurine; platinum; platinum analogs or platinum-based analogs such as cisplatin, oxaliplatin and carboplatin; vinblastine (VELBAN); etoposide (VP-16); ifosfamide; mitoxantrone; vincristine (ONCOVIN); vinca alkaloid; vinorelbine (NAVELBINE); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN) combined with 5-FU and leucovorin.

Anti-hormonal agents that act to regulate or inhibit hormone action on tumors and/or suppress ovarian function include anti-estrogens and selective estrogen receptor modulators (SERMs), including, for example, tamoxifen (NOLVADEX), raloxifene, droloxifene, 4-hydroxytamoxifen, trioxifene, keoxifene, LY117018, onapristone, and FARESTON toremifene; aromatase inhibitors; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in aberrant cell proliferation, such as, PKC-alpha, Raf, H-Ras, and epidermal growth factor receptor (EGF-R); vaccines such as gene therapy vaccines, for example, ALLOVECTIN vaccine, LEUVECTIN vaccine, and VAXID vaccine; PROLEUKIN rIL-2; LURTOTECAN topoisomerase 1 inhibitor; ABARELIX rmRH; and pharmaceutically acceptable salts, acids or derivatives of any of the above. In these methods, the anti-hormonal agent may be tamoxifen.

A "taxane" is a chemotherapy which inhibits mitosis and interferes with microtubules. Examples of taxanes include Paclitaxel (TAXOL); cremophor-free, albumin-engineered nanoparticle formulation of paclitaxel or nab-paclitaxel (ABRAXANE); and Docetaxel (TAXOTERE).

An "anthacycline" is a type of antibiotic that comes from the fungus Streptococcus peucetius, examples include: Daunorubicin, Doxorubicin, and Epirubicin, etc. "Anthracycline-based chemotherapy" refers to a chemotherapy regimen that consists of or include one or more anthracycline. Examples include 5-FU, epirubicin, and cyclophosphamide (FEC); 5-FU, doxorubicin, and cyclophosphamide (FAC); doxorubicin and cyclophosphamide (AC); epirubicin and cyclophosphamide (EC); etc.

For the purposes herein, "carboplatin-based chemotherapy" refers to a chemotherapy regimen that consists of or includes one or more Carboplatins. An example is TCH (Docetaxel/TAXOL, Carboplatin, and Trastuzumab/HERCEPTIN).

An "aromatase inhibitor" inhibits the enzyme aromatase, which regulates estrogen production in the adrenal glands. Examples of aromatase inhibitors include: 4(5)-imidazoles, aminoglutethimide, MEGASE megestrol acetate, AROMASIN exemestane, formestanic, fadrozole, RIVISOR vorozole, FEMARA letrozole, and ARIMIDEX anastrozole. In these methods, the aromatase inhibitor may be one or more of letrozole, anastrozole, and exemestane.

A "cyclin-dependent kinases 4 and 6 inhibitor", also referred to as a "CDK4/6 inhibitor", inhibits CDK4 and CDK6 enzymes. Examples of CDK4/6 inhibitor include: abemaciclib, palbociclib, and ribociclib A "phosphoinositide 3-kinase inhibitor", also referred to as a "PI3K inhibitor", inhibits one or more phosphoinositide 3-kinase enzymes, which are part of the PI3K/AKT/mTOR pathway. Examples of PI3K inhibitors include: alpelisib, idelalisib, and buparlisib.

A "mammalian target of rapamycin inhibitor", also referred to as a "mTOR inhibitor", inhibits the mammalian target of rapamycin (mTOR), which is a serine/threonine-specific protein kinase that belongs to the family of phosphatidylinositol-3 kinase (PI3K) related kinases (PIKKs). Examples of mTOR inhibitors include: temsirolimus, sirolimus, everolimus, and ridaforolimus.

An "antimetabolite chemotherapy" is use of an agent which is structurally similar to a metabolite, but cannot be used by the body in a productive manner. Many antimetabolite chemotherapy interferes with the production of the nucleic acids, RNA and DNA. Examples of antimetabolite chemotherapeutic agents include gemcitabine (GEMZAR), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U), dacarbazine (DTIC-DOME), azocytosine, deoxycytosine, pyridmidene, fludarabine (FLUDARA), cladrabine, 2-deoxy-D-glucose, etc.

By "chemotherapy-resistant" cancer is meant that the cancer patient has progressed while receiving a chemotherapy regimen (i.e., the patient is "chemotherapy refractory"), or the patient has progressed within 12 months (for instance, within 6 months) after completing a chemotherapy regimen.

The term "platin" is used herein to refer to platinum-based chemotherapy, including, without limitation, cisplatin, carboplatin, and oxaliplatin.

The term "fluoropyrimidine" is used herein to refer to an antimetabolite chemotherapy, including, without limitation, capecitabine, floxuridine, and fluorouracil (5-FU).

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m2 dose, but rather as an absolute amount of the therapeutic agent.

A "loading" dose herein generally comprises an initial dose of a therapeutic agent administered to a patient and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dosc(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every month, approximately every 2 months, approximately every 3 months, or approximately every 4 months, preferably every 3 months.

"Infusion" or "infusing" refers to the introduction of a drug-containing solution into the body through a vein for therapeutic purposes. Generally, this is achieved via an intravenous (IV) bag.

A "package insert" is a leaflet that, by order of the Food and Drug Administration (FDA) or other Regulatory Authority, must be placed inside the package of every prescription drug. The leaflet generally includes the trademark for the drug, its generic name, and its mechanism of action; states its indications, contraindications, warnings, precautions, adverse effects, and dosage forms; and includes instructions for the recommended dose, time, and route of administration.

The phrase "safety data" concerns the data obtained in a controlled clinical trial showing the prevalence and severity of adverse events to guide the user regarding the safety of the drug, including guidance on how to monitor and prevent adverse reactions to the drug.

"Efficacy data" refers to the data obtained in controlled clinical trial showing that a drug effectively meets primary clinical endpoints, such as by achieving a particular pharmacokinetic endpoint in a satisfactory percentage of subjects (e.g., suppression of estradiol levels), or in some examples, treats a disease, such as cancer.

By "stable mixture" when referring to a mixture of two or more drugs, means that each of the drugs in the mixture essentially retains its physical and chemical stability in the mixture as evaluated by one or more analytical assays. Exemplary analytical assays for this purpose include: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay.

A "monotherapy" is therapy that uses one type of treatment, such as radiation therapy or surgery alone, to treat a certain disease or condition, or in drug therapy, it refers to the use of a single medicament or modality to treat a disease or condition.

A "combination therapy" is a therapy that uses more than one type of treatment such as radiation therapy or surgery, to treat a certain disease or condition, or in drug therapy, it refers to the use of more than one medicament or modality to treat a certain disease or condition.

A drug that is administered "concurrently" with another type of treatment or one or more other drugs is administered during the same treatment cycle as the other treatments or drugs such that the patient receives the effects of both drugs and/or therapies during the treatment cycle. In the methods of this disclosure, a treatment cycle for a breast cancer patient may be 3 months in length, and the drugs and/or therapies administered concurrently with the leuprolide formulations of this disclosure may include, without limitation, one or more of endocrine therapies such as selective estrogen receptor modulators (SERMs; such as Tamoxifen, Toremifene, Raloxifene, Ospemifene, and Bazedoxifene), selective estrogen receptor degraders (SERDs; such as fulvestrant), aromatase inhibitors (AIs; such as anastrozole, letrozole, exemestane, vorozole, formestane, and fadrozole); mammalian target of rapamycin (mTOR) inhibitors; such as temsirolimus, sirolimus, everolimus, and ridaforolimus); Phosphatidylinositol 3-kinases inhibitors (PI-3 kinase or PI3K; such as alpelisib, idelalisib, and buparlisib); cyclin-dependent kinases 4 and 6 inhibitors (CDK4/6 inhibitors; such as abemaciclib, palbociclib, and ribociclib); chemotherapy; immuno-therapy, gene therapy, radiation therapy; and surgery.

Leuprolide Compositions

Leuprolide is a synthetic nonapeptide that is a potent gonadotropin-releasing hormone receptor (GnRHR) agonist (an LHRH agonist analog) approved in the United States and other countries for the palliative treatment of prostate cancer, endometriosis, uterine fibroids, central precocious puberty, and in vitro fertilization techniques. As its basic mechanism, leuprolide suppresses gonadotrope secretion of luteinizing hormone and follicle-stimulating hormone that subsequently suppresses gonadal sex steroid production. With continued use, leuprolide causes pituitary desensitizing and down-regulation to affect the pituitary-gonadal axis, leading to suppressed circulating levels of luteinizing and sex hormones. The use of leuprolide products in one condition does not indicate that this same active ingredient, delivery system, or dose will be effective in another condition, nor that it will provide a similar benefit at all. Clinicians consider a treatment to be effective when it provides a positive benefit across defined outcomes applicable to the specific patient population in a specific condition.

Biodegradable polymers have been employed in many medical applications, including drug delivery devices. The drug is generally incorporated into the polymeric composition and formed into the desired shape outside the body. This solid implant is then typically inserted into the body of a subject through an incision. Alternatively, small discrete particles (microspheres) composed of these polymers can be injected into the body by a syringe. Certain of these polymers can be injected via syringe as a flowable polymeric composition that forms a solid or semi-solid implant in situ. Exemplary polymeric compositions of leuprolide for reducing serum testosterone levels for treating prostate cancer in a male patient are described in detail in U.S. Pat. No. 9,254,307, issued Feb. 9, 2016, which is incorporated herein, in its entirety, by this reference.

Leuprolide microsphere products are difficult to manufacture, and they all require a deep intramuscular (i.m.) injection using large volumes of fluid to ensure that all the microspheres are properly administered to the patient. These injections are often very painful and lead to tissue damage.

Currently, there is no leuprolide-based extended release formulation approved for use in human subjects with hormone receptor-positive breast cancer which requires administration only once per about three months and/or which provides dosing of leuprolide at a level of up to about 10 mg/mL leuprolide per month. The three month dosing period for the product of the present invention would be beneficial to both patients and physicians as it would provide a significant reduction in the frequency of injections (considering adjuvant endocrine therapy is recommended for 5 years) and increased confidence that estradiol (E2) will be effectively suppressed. Additionally, the present invention's combination of a higher active drug dose within a 3-monthly polymeric delivery system is expected to result in higher exposure to drug than has previously been available to breast cancer patients, thus reducing potential for escapes in E2 above post-menopausal levels throughout the dosing period. Finally, the subcutaneous delivery route of the leuprolide-based extended release formulations of this disclosure will improve patient tolerability/compliance and increased flexibility of injection sites compared to current utilization of GnRH agonists in microsphere formulations that are provided by deep intramuscular injection in large volumes.

The flowable, extended release compositions suitable for use in the methods of this disclosure, which may also be referred to as controlled release compositions, may be used to provide a biodegradable or biocrodible microporous in situ formed implant or depot in a subject. The flowable composition is composed of a biodegradable thermoplastic polymer or copolymer in combination with a suitable organic solvent. The biodegradable thermoplastic polyesters or copolymers are substantially insoluble in water and body fluid, biocompatible, and biodegradable and/or biocrodible within the body of a subject. The flowable composition is administered as a liquid or gel to tissue wherein a solid or semi-solid implant is formed in situ upon dissipation of the solvent. The composition is biocompatible and the polymer matrix does not cause substantial tissue irritation or necrosis at the implant site. The implant so formed is optimally used to deliver leuprolide or pharmaceutically acceptable salts or analogs thereof (e.g., leuprolide acetate) in a controlled, or extended, release manner to the subject over a period of between about 30 and about 120 days, preferably about 90 days.

The flowable, extended release composition can be a liquid or a gel, suitable for injection in a patient (e.g., human). As used herein, "flowable" refers to the ability of the composition to be injected through a medium (e.g., syringe) into the body of a patient. For example, the composition can be injected, with the use of a syringe, beneath the skin of a patient (i.e., subcutaneously). The ability of the composition to be injected into a patient will typically depend upon the viscosity of the composition. The composition will therefore have a suitable viscosity prior to injection, such that the composition can be forced through the medium (e.g., syringe) into the body of a patient. The composition may be administered by injection though a syringe with a 6 to 32 or larger gauge needle, preferably an 18 to 30 gauge needle, or, in other cases, may be administered by injection using an autoinjector. As used herein, a "liquid" is a substance that undergoes continuous deformation under a shearing stress.

The flowable, extended release compositions useful in the methods of this disclosure are thermoplastic compositions in which a solid, biodegradable polyester and leuprolide acetate are dissolved in a biocompatible polar aprotic solvent to form a flowable composition, which can then be administered via a syringe and needle. Any suitable biodegradable thermoplastic polyester can be employed, provided the biodegradable thermoplastic polyester is at least substantially insoluble in aqueous medium or body fluid. Suitable biodegradable thermoplastic polyesters are disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. Preferably, the suitable biodegradable thermoplastic polyester is a polylactide, a polyglycolide, a copolymer thereof, a terpolymer thereof, or a combination thereof.

The type, molecular weight, and amount of biodegradable thermoplastic polyester present in the composition will typically depend upon the desired properties of the extended release implant. For example, the type, molecular weight, and amount of biodegradable thermoplastic polyester can influence the length of time in which the leuprolide is released from the extended release implant. Specifically, one embodiment of the present invention is a three-month delivery system of leuprolide acetate (i.e., a formulation that requires administration only once per about three months). In such an embodiment, the biodegradable thermoplastic polyester can preferably be poly (DL-lactide-co-glycolide) (PLG) without a carboxylic acid terminal group, comprising a lactide to glycolide monomer molar ratio from about 70:30 to about 80:20, or 85:15, and preferably comprising a lactide to glycolide monomer molar ratio of about 75:25. The biodegradable polymer can be present from about 35 wt. % to about 60 wt. % of the composition and can have a weight average molecular weight from about 15 kDa to about 45 kDa, inclusive, or about 15 kDa to about 26 kDa, inclusive, or from about 17 kDa to about 21kDa, inclusive.

In these PLG polymers, the terminal groups of the poly (DL-lactide-co-glycolide) can either be hydroxyl or ester depending upon the method of polymerization. Ring-opening polymerization of the cyclic lactide or glycolide monomers with water, lactic acid, or glycolic acid will provide polymers with the same terminal groups. However, ring-opening of the cyclic monomers with a monofunctional alcohol such as methanol, ethanol, or 1-dodecanol will provide a polymer with one hydroxyl group and one ester terminal groups. Ring-opening polymerization of the cyclic monomers with a diol such as 1,6-hexanediol or polyethylene glycol will provide a polymer with only hydroxyl terminal groups. Preferably, the PLG polymers used in the methods of this disclosure are formed using ring-opening polymerization of the cyclic monomers with 1,6-hexanediol and therefore have only hydroxyl terminal groups.

Any suitable solvent can be employed, provided the solvent is miscible to dispersible in aqueous medium or body fluid. Suitable solvents are disclosed, e.g., in Aldrich Handbook of Fine Chemicals and Laboratory Equipment, Milwaukee, Wis. (2000); U.S. Pat. Nos. 5,324,519; 4,938,763; 5,702,716; 5,744,153; and 5,990,194. The solvent should be able to diffuse into body fluid so that the flowable composition coagulates or solidifies. The solvent may or may not dissolve the polymer. Preferred solvents for the biodegradable polymer are non-toxic and otherwise biocompatible. Suitable solvents may comprise one or more solvents selected from the group consisting of amides, acids, alcohols, esters of monobasic acids, ether alcohols, sulfoxides, lactones, polyhydroxy alcohols, esters of polyhydroxy alcohols, ketones, and ethers. Preferably, the solvent is an organic solvent selected from at least one of N-methyl-2-pyrrolidone (NMP), acetone, cyrene, butyrolactone, ε-caprolactone, caprolactam, N-cycylohexyl-2-pyrrolidone, diethylene glycol monomethyl ether, dimethylacetamide, N,N-dimethyl formamide, dimethyl sulfoxide (DMSO), ethyl acetate, ethyl lactate, N-ethyl-2-pyrrolidone, glycerol formal, glycofurol, N-hydroxyethyl-2-pyrrolidone, isopropylidene glycerol, lactic acid, methoxypolyethylene glycol, methoxypropyleneglycol, methyl acetate, methyl ethyl ketone, methyl lactate, benzyl benzoate (BnBzO), polysorbate 80, polysorbate 60, polysorbate 40, polysorbate 20, polyoxyl 35, polyethylene glycol (PEG), hydrogenated castor oil, polyoxyl 40 hydrogenated castor oil, sorbitan monolaurate, sorbitan monostearate, sorbitan monooleate, benzyl alcohol, n-propanol, isopropanol, tert-butanol, propylene carbonate, propylene glycol, 2pyrrolidone, α-tocopherol, triacetin, tributyl citrate, acetyl tributyl citrate, acetyl triethyl citrate, triethyl citrate, esters thereof, and combinations thereof. Preferably, the solvent is N-methyl-2-pyrrolidone (NMP).

The solvent can be present in any suitable amount, provided the solvent is miscible to dispersible in aqueous medium or body fluid. The type and amount of solvent present in the composition will typically depend upon the desired properties of the extended release implant. For example, the type and amount of solvent can influence the length of time in which the leuprolide is released from the extended release implant. For example, the composition can be used to formulate a three-month polymer delivery system of leuprolide acetate. In such system, the biocompatible polar aprotic solvent, N-methyl-2-pyrrolidone, is preferably present in about 50 wt. % to about 60 wt. % of the composition.

Thus, the flowable, extended release compositions useful in the methods of this disclosure may comprise an organic solvent, leuprolide or a pharmaceutically acceptable salt or analog thereof, and a biodegradable polymer. Pharmaceutically acceptable salts or analogs of leuprolide include leuprolide acetate, leuprolide monoacetate, leuprolide oleate, leuprolide palmitate, leuprolide mesylate, leuprolide trifluoracetic acid (TFA), leuprolide trifluoroacetate, leuprolide (5-9), (D-His2)-leuprolide trifluoracetic acid (TFA), leuprolide hydrochloric acid (HCL), leuprolide-D5 acetate, and combinations thereof. The sequences and chemical structures of any of these leuprolide salts are readily known and available. A particularly preferred pharmaceutically acceptable salt of leuprolide is leuprolide acetate.

In some embodiments, the biodegradable polymer may be a poly lactide-co-glycolide) (PLG) copolymer comprising a lactide to glycolide monomer molar ratio from about 70:30 to about 80:20, wherein the polymer has substantially no titratable carboxylic acid groups and wherein at least one distal end group of the polymer is hydroxyl-terminated. Preferably, the biodegradable polymer comprises 75:25 poly (lactide-co-glycolide) copolymer segments, wherein the polymer has substantially no titratable carboxylic acid groups and wherein at least one distal end group of the polymer is hydroxyl-terminated. The biodegradable polymer may comprise 85:15 poly(lactide-co-glycolide) copolymer segments, wherein the polymer has substantially no titratable carboxylic acid groups and wherein at least one distal end group of the polymer is hydroxyl-terminated.

The biodegradable polymer may have a weight average molecular weight from about 12 kDa to about 45 kDa, or weight average molecular from about 15 kDa to about 45 kDa, from about 15 kDa to about 26 kDa, from about 15 kDa to about 21 kDa, from about 19 kDa to about 26 kDa, or from about 17 kDa to about 21 kDa, inclusive. Preferably, the biodegradable polymer has a weight average molecular weight from any whole number to any other whole number from about 12 kDa to about 45 kDa, inclusive.

The polymer may have the chemical Formula:

$$HO—(P)—C(=O)O—Ra—O(O=)C—(P)—OH,$$

wherein Ra is an alkane diradical comprising about 4 to about 8 carbons and is a residue of an alkane diol, and P is a polymeric segment of repeating units of lactide, glycolide, or co(lactide-glycolide).

A polymer of the present invention can be represented structurally as a compound of Formula (I):

(I)

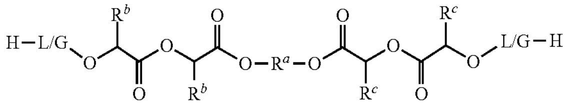

wherein "L/G" signifies a PLG copolymer segment, the H atoms at both distal ends signify the hydrogen atoms borne by the terminal hydroxyl groups, and $R^a$ is an alkane diradical. The $R^b$ and $R^c$ groups shown on either side of the $R^a$ core moiety may be either hydrogen or methyl, with the proviso that both $R^b$ groups are either hydrogen or methyl concurrently, and both $R^c$ groups are either hydrogen or methyl concurrently, but $R^b$ and $R^c$ need not be the same.

The groups indicated as "L/G" in Formula (I) thus signify lactide/glycolide copolymer segments of the structure:

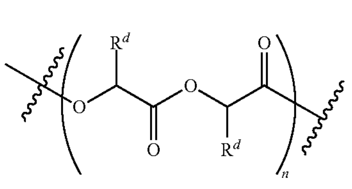

wherein the $R^d$ groups are independently hydrogen or methyl, again with the proviso that as described above, hydrogen substituents or methyl substituents are generally found in pairs due to their incorporation in pairs as repeating units from the dimeric lactide or glycolide reagents. Other than this requirement of $Ra^d$ groups generally being in pairs, methyl groups and hydrogen groups are arranged randomly throughout the copolymer segments L/G, with the understanding that due to the higher rate of reaction of G-G groups, these will tend to be more frequently found adjacent to $R^a$. The wavy lines signify points of attachment to other radicals, for example hydrogen atoms at the distal ends and the core alkanediol hydroxyl groups at the proximal ends. The number of repeating units, n, range from about 20 up to about 750 for each copolymer segment, providing a polymer of a weight average molecular weight of about 6 kDa ranging up to about 200 kDa in weight. It is understood that the two L/G copolymer segments need not be identical, and likely are not identical, either in sequence or in the molecular weight of each copolymer segment in a given polymer molecule. Further, the specific composition of each molecule within a sample of the polymer varies in the same manner.

Yet another polymer of the present invention can be represented structurally as a compound of Formula (II):

(II)

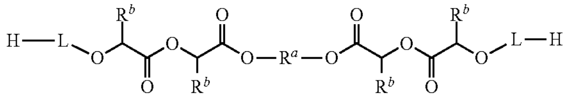

wherein L signifies a polylactide or polylactate polymer segment, the H atoms at both distal ends signify the hydrogen atoms borne by the hydroxyl groups, and $R^a$ is an alkane diradical. The $R^b$ groups on either side of the $R^a$ core moiety are all methyl.

As is described above, in the polymers of formulas (I) and (II), the distal ends of the copolymer segments comprise hydroxyl groups. The proximal ends of the copolymer segments therefore comprise the carboxyl moieties at the opposite end of the lactide or the glycolide repeating unit, which are linked in ester bonds with hydroxyl groups of the core alkanediols. This structural element results in the lack of titratable carboxylic acid groups in a polymer of the invention, the product being a neutral polymer.

The core alkanediol can be an α,ω-diol to which the copolymer segments are bonded via the two primary hydroxyl groups. Specific examples of α,ω-diols include 1,4-butanediol, 1,5-pentanediol, 1,6-hexanediol, 1,7-heptanediol, and 1,8-octanediol. A particularly preferred alkanediol is 1,6-hexanediol.

The polymer of Formula (I) may be formed by a polymerization reaction wherein the core alkanediol comprising $R^a$ serves as the initiator for the ring-opening polymerization of the lactide and glycolide reagents. The molar percent, and thus the weight percentage, of the alkanediol that is present in the polymerization reaction has an influence on the molecular weight of the biodegradable polymer that is formed. Use of a higher percentage of the alkanediol in the polymerization reaction provides, on the average, a polymer of lower molecular weight that has relatively shorter PL or PLG copolymer segments linked to the alkanediol core.

A preferred embodiment according to the present invention is a method of preparation of a polymer of Formula (I), comprising contacting an alkanediol, glycolide, lactide, and a catalyst, the catalyst being adapted to catalyze the ring-opening polymerization of the lactide and the glycolide initiated on the alkanediol.

A polymer of the present invention comprising PLG copolymer segments is preferably prepared using a catalyst suitable for ring-opening polymerization of lactide and glycolide. The catalyzed ring opening reaction initially takes place between the lactide or glycolide reagent and a hydroxyl group of the alkanediol core unit such that the lactide or a glycolide unit forms an ester bond. Thus, after the first step of polymerization, only hydroxyl groups on the growing polymer chain continue to be available for further lactide or glycolide addition. As polymerization continues, each step continues to result in formation only of hydroxyl-terminated copolymer segments attached to the alkanediol. In this manner, polymerization takes place until the supply of lactide and glycolide reagents is exhausted, producing the hydroxyl group terminated polymer. It is understood that a polymer of the present invention comprising PL copolymer segments can be made in the same manner, only omitting the glycolide reagent.

The alkanediol can be an α,ω-diol such as 1,6-hexanediol. The alkanediol may be present in the polymerization reaction mixture in amounts ranging from about 0.05 wt. % to about 5.0 wt. %, preferably from about 0.5 wt. % to about 2.0 wt. %.

The catalyst may be any catalyst suitable for ring-opening polymerization, but a preferred catalyst is a tin salt of an organic acid. The tin salt may be either in the stannous (divalent) or stannic (tetravalent) form. A particularly preferred catalyst is stannous octanoate. The catalyst may be present in the polymerization reaction mixture in any suitable amount, typically ranging from about 0.01 wt. % to 1.0 wt. %.

The polymerization reaction may be carried out under a variety of conditions of temperature, time and solvent. Alternatively, solvent may be absent and the polymerization be carried out in a neat melt. The polymerization reaction wherein the reactants comprise an alkanediol (such as hexane-1,6-diol), lactide, and glycolide in defined proportions by weight, and a catalyst such as stannous octanoate, is preferably carried out as a neat melt in the absence of oxygen at elevated temperature for a period of at least several hours. Preferably, the reaction is carried out at about 140° C., either under vacuum or an atmosphere of inert gas, such as nitrogen.

The weight percent, and thus mole percent, of lactide or glycolide repeating units in the polymer can be varied by altering the weight percentages of the two reactants present in the polymerization reaction mixture. The properties of the polymer can be changed by variations in the ratio of the lactide to the glycolide monomer components, and by the percent of the alkanediol initiator that is present.

Specifically, the molecular weight range of the polymer can be controlled by the amount of core alkanediol present in the polymerization reaction relative to the amounts of lactide and glycolide. The greater the weight percentage, and thus the greater the mole fraction of the alkanediol in the polymerization reaction mixture, the shorter the chain lengths of the polymers attached to the alkanediol core due to the decreased availability of lactide or glycolide reagent molecules per initiating hydroxyl group.

Another polymer of this disclosure comprises the chemical structure:

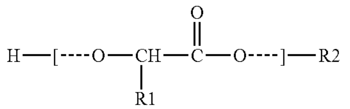

wherein R1 is H or $CH_3$; R2 is an alkyl group; and, wherein the polymer has substantially no titratable carboxylic acid groups.

A "titratable carboxylic acid group" as used herein refers to a carboxylic acid group in free form, that is, not bound as an ester or other derivative, wherein the carboxylic acid group can bear a free proton which may dissociate (ionize) in aqueous solution to form a carboxylate anion and a proton (acid). Therefore, an organic polymer with no titratable carboxylic acid groups is not an acidic polymer, and all carboxylate moieties within the polymer are bonded into esters, amides, or other non-acidic derivatives.

The solubility of the biodegradable thermoplastic polyesters in various solvents will differ depending upon their composition, their crystallinity, their hydrophilicity, hydrogen-bonding, and molecular weight. It has also been found that solutions containing very high concentrations of high-molecular-weight polymers sometimes coagulate or solidify slower than more dilute solutions. It is suspected that the high concentration of polymer impedes the diffusion of solvent from within the polymer matrix and consequently prevents the permeation of water into the matrix where it can precipitate the polymer chains. Thus, there is an optimum concentration at which the solvent can diffuse out of the polymer solution and water penetrates within to coagulate the polymer.

In the flowable, extended release compositions useful in the methods of this disclosure, leuprolide is preferably present as the acetate salt (i.e., leuprolide acetate), although other pharmaceutically acceptable salts or analogs of leuprolide are disclosed herein and expressly contemplated for use in the present invention. The leuprolide salt is, in some embodiments, lyophilized prior to use. Typically, the leuprolide salt can be dissolved in an aqueous solution, sterile filtered, and lyophilized in a syringe. The polymer/solvent solution can be filled into another syringe. The two syringes can then be coupled together, and the contents can be transferred back and forth between the two syringes until the polymer/solvent solution and the leuprolide acetate are effectively mixed together, forming a flowable composition. The flowable composition can be drawn into one syringe. The two syringes can then be disconnected. Alternatively, the lyophilized leuprolide salt or a leuprolide/solvent solution, and a polymer/solvent solution, can be contained in a dual chamber syringe, and the contents of the two chambers are mixed to form a flowable composition. A needle can be inserted onto the syringe containing the flowable composition. As another alternative, the polymer, solvent, and leuprolide salt can be formulated into a single syringe. The flowable composition can then be injected through the needle into the body. The flowable composition can be formulated and administered to a patient as described in, e.g., U.S. Pat. Nos. 5,324,519; 4,938,763; 5,702,716; 5,744,153; and 5,990,194; or as described herein. Once in place, the solvent dissipates, the remaining polymer solidifies, and a solid or semi-solid structure or depot is formed. The solvent dissipates and the polymer solidifies and entraps or encases the leuprolide salt within the solid or semi-solid matrix.

To form exemplary flowable, extended release compositions useful in the methods of this disclosure, poly(DL-lactide-co-glycolide) with a molar ratio of lactide to glycolide of 75:25may be dissolved in NMP to give a solution with 45% by weight polymer. This solution may be filled into 3.0 cc polypropylene syringes with a male luer lock fitting and terminally sterilized by exposure to gamma irradiation at 23.2-24.6 kilograys or by exposure to e-beam irradiation. The polymer weight average molecular weight after irradiation may be 15,094 daltons. The leuprolide acetate may be dissolved in water, sterile filtered through a 0.2 cm filter and filled into a polypropylene or cyclic olefin-based syringe with a male luer lock fitting. The aqueous solution may be frozen and the water removed by vacuum to yield a lyophilized cake of leuprolide. Immediately prior to administration to a subject, these two syringes may be connected together with a coupler and the contents of the two syringes mixed by moving the material back and forth between the two syringes to provide a reconstituted product with, for example, about 4-8% by weight of leuprolide acetate. The product may then be pulled into the syringe with the male luer lock fitting and a one-half inch 20-gauge needle attached for injection into the subject, preferably subcutaneous injection.

The release of leuprolide acetate from these solid or semi-solid implants will follow the same general rules for release of a drug from a monolithic polymeric device. The release of leuprolide acetate can be affected by the size and shape of the implant, the loading of leuprolide acetate within the implant, the permeability factors involving the leuprolide acetate and the particular polymer, and the degradation of the polymer.

The amount of leuprolide acetate incorporated into the flowable, in situ, solid forming implant depends upon the desired release profile, the concentration of leuprolide acetate required for the desired biological effect, and the length of time that the leuprolide acetate will be released into the subject for treatment. There is no critical upper limit on the amount of leuprolide acetate incorporated into the polymer solution except for that of an acceptable solution or dispersion viscosity for injection through a syringe needle. The lower limit of leuprolide acetate incorporated into the delivery system is dependent simply upon the activity of the leuprolide acetate and the length of time needed for treatment and the disease to be treated. Specifically, in exemplary embodiments of this disclosure, the composition may be used to formulate a three-month delivery system of leuprolide acetate, in which the leuprolide acetate can preferably be present in about 4 wt. % to about 8 wt. % of the composition, or a total amount of leuprolide acetate, or leuprolide base equivalents, between about 22 mg and about 40 mg. Preferably the amount of leuprolide acetate ranges from about 28 mg to about 32 mg, and is more preferably about 30 mg. The solid or semi-solid implant formed from the flowable composition will release the leuprolide acetate contained within its matrix at a controlled rate until the leuprolide acetate is effectively depleted.

These compositions can be used to formulate a three-month delivery system of leuprolide acetate, in which less than about 1.0 mL, preferably less than about 0.50 mL inclusive, preferably about 0.30 mL to about 0.50 mL, or more preferably about 0.375 mL, of the flowable composition may be administered to the subject as a single dose, preferably subcutaneously.

Articles of Manufacture

This disclosure also provides articles of manufacture or kits according to the polymeric compositions and mixing and administration methods described above. An exemplary article of manufacture of this disclosure may include a container of the extended release leuprolide composition of this disclosure, described above. The container may be a single syringe. In these articles of manufacture, the syringe may contain about 26 mg to about 30 mg of leuprolide free base equivalent, preferably about 28 mg of leuprolide free base equivalent (e.g., about 28 mg to about 32 mg of leuprolide acetate, preferably about 30 mg of leuprolide acetate). In these articles, the syringe may contain less than about 1.0 mL of the extended release composition, preferably less than about 0.5 mL of the extended release composition, preferably about 0.30 mL to about 0.50 mL of the extended release composition, or more preferably about 0.375 mL of the extended release composition. In these articles, the biodegradable polymer may be a poly (lactide-co-glycolide) copolymer comprising a lactide to glycolide monomer molar ratio from about 70:30 to about 80:20, wherein the polymer has substantially no titratable carboxylic acid groups and wherein at least one distal end group of the polymer is hydroxyl-terminated. In these articles, the biodegradable polymer may preferably be a poly (lactide-co-glycolide) comprising a lactide to glycolide monomer molar ratio of 75:25, wherein the polymer has substantially no titratable carboxylic acid groups and wherein at least one distal end group of the polymer is hydroxyl-terminated. In these articles, the biodegradable polymer may preferably be a poly (lactide-co-glycolide) comprising a lactide to glycolide monomer molar ratio of 85:15, wherein the polymer has substantially no titratable carboxylic acid groups and wherein at least one distal end group of the polymer is hydroxyl-terminated. The biodegradable polymer may be present from about 35 wt. % to about 60 wt. % of the composition and have a weight average molecular weight of from about 12 kDa to about 45 kDa. The biodegradable polymer may have a weight average molecular weight from about 15 kDa to about 45 kDa, from about 15 kDa to about 26 kDa, from about 15 kDa to about 21 kDa, from about 19 kDa to about 26 kDa, or from about 17 kDa to about 21 kDa, inclusive. In some embodiments, the biodegradable polymer has a weight average molecular weight from any whole number to any other whole number from about 12 kDa to about 45 kDa, inclusive. The organic solvent may be N-methyl-2-pyrrolidone (NMP).

Another exemplary article of manufacture according to this disclosure may include a first container comprising a lyophilized salt (e.g., leuprolide acetate) or a leuprolide/solvent solution and a second container comprising a solution comprising a biodegradable polymer and organic solvent, and instructions for combining and/or mixing the contents of the first and second containers to form a flowable, extended release composition for administration to a subject. In these articles, the first and second containers may be first and second chambers of a dual chamber single syringe. The contents of the first and second chambers may be combined within the syringe by adding the contents of second chamber into the first chamber, followed by mixing the polymer solution and the leuprolide to form a flowable composition. Alternatively, the contents of the first chamber may be added to the second chamber followed by mixing to form a flowable composition. In these articles of manufacture, the first chamber may contain about 26 mg to about 30 mg of a leuprolide free base equivalent, preferably about 28 mg of leuprolide free base equivalent (e.g., about 28 mg to about 32 mg of leuprolide acetate, preferably about 30 mg of leuprolide acetate), and the second chamber may contain less than about 1.0 mL of the biodegradable polymer/organic solvent composition, preferably less than about 0.5 mL of the biodegradable polymer/organic solvent composition, preferably about 0.30 mL to about 0.50 mL of the biodegradable polymer/organic solvent composition, or more preferably about 0.375 mL of the biodegradable polymer/organic solvent composition.

In these articles, the first and second containers may be first and second syringes, of a two-syringe system, respectively. The contents of the first and second syringes may be combined by coupling the syringes together, transferring the contents back and forth between the two syringes until the polymer/solvent solution and the leuprolide are effectively mixed together to form a flowable composition. In these articles, the first syringe may contain about 26 mg to about 30 mg of leuprolide free base equivalent, preferably about 28 mg of leuprolide free base equivalent (e.g., about 28 mg to about 32 mg of leuprolide acetate, preferably about 30 mg of leuprolide acetate). In these articles of manufacture, the second syringe may contain less than about 1.0 mL of the biodegradable polymer/organic solvent composition, preferably less than about 0.5 mL, preferably about 0.30 mL to about 0.50 mL of the biodegradable polymer/organic solvent composition, or more preferably about 0.375 mL of the biodegradable polymer/organic solvent composition.

These articles of manufacture may further include a needle adapted to be inserted onto a syringe containing the flowable leuprolide composition for subcutaneous administration of the flowable leuprolide composition to a subject. Optionally, the flowable leuprolide composition is stable for at least, or up to 30 minutes at 25 degrees C. Stability of the flowable leuprolide composition can be evaluated by one or more assays selected from the group consisting of: color, appearance and clarity (CAC), concentration and turbidity analysis, particulate analysis, size exclusion chromatography (SEC), ion-exchange chromatography (IEC), capillary zone electrophoresis (CZE), image capillary isoelectric focusing (iCIEF), and potency assay.

These articles of manufacture may further comprise instructions for the use thereof for suppression of ovarian function in a subject with HR-positive breast cancer. These articles of manufacture may also comprise a package insert that provides efficacy and/or safety data for the use of leuprolide in the suppression of ovarian function in a subject with HR-positive breast cancer, who is concurrently treated with a therapeutic treatment for the cancer.

Treatment Methods

The stages of breast cancer are based on a number of factors, such as the size of the tumor, if cancer is found in the lymph nodes, and how far the cancer has spread. The stages are numbered 0, I, II, III, or IV, with Stage I being the least advanced stage and Stage IV being the most advanced. Stage 0 is considered non-invasive breast cancer. Stages I-II is considered carly breast cancer. Stage III is considered locally advanced breast cancer. Stage IV is considered metastatic breast cancer. These descriptions are broad descriptions of breast cancer stages and may not include all possibilities. The methods of this disclosure may can be used to suppress ovarian function in a subject with hormone receptor-positive breast cancer at any stage, including Stages 0, I, II, III or IV, and substages of these.

Stages I, IIA, and IIB (and some cancers of stage IIIA) are considered carly breast cancer. At these stages, the cancer has not spread beyond the breast or the axillary lymph nodes (those under the arm).

Locally advanced breast cancer includes Stages IIIA, IIIB, and IIIC. Stage IIIA breast cancer includes instances when the tumor size is not large but the cancer has spread to many axillary (under the arm) lymph nodes or lymph nodes near the breastbone. Stage IIIA breast cancer includes instances when the tumor is large but there is less lymph node spread. Stage IIIB describes breast cancer in which the tumor has spread to the chest wall or the skin of the breast and may or may not have spread to lymph nodes. Stage IIIC describes cancer that has spread to lymph nodes below or above the collarbone, to many axillary (under the arm) lymph nodes, or to lymph nodes near the breastbone. The tumor may be of any size.

Stage IV describes metastatic breast cancer, which is cancer that has spread from the breast to other parts of the body, such as the bones or the liver, lungs, or brain (visceral metastases).

In premenopausal women, approximately 60% of breast tumors are HR-positive and can benefit from suppression of estrogen by surgical, radiological, or pharmacological means. Traditional medical treatment with ovarian ablation or suppression by radiation or oophorectomy permanently eliminates the possibility of future fertility. Alternatively, the use of adjuvant endocrine therapies (also referred to as "hormone therapies"), such as selective estrogen receptor modulators (SERMs), selective estrogen receptor degraders (SERDs), and drugs that decrease release of endogenous non-ovarian estrogen (such as aromatase inhibitors), suppress estrogen production temporarily, preserving the possibility of future pregnancy. These drugs may be combined with gonadotropin-releasing hormone (GnRH) agonists or antagonists, such as leuprolide, to induce and maintain ovarian suppression. Gonadotropin-releasing hormone (also commonly referred to luteinizing hormone-releasing hormone (LHRH)) agonists mimic the effect of GnRH by promoting release of the gonadotropins follicle-stimulating hormone (FSH) and luteinizing hormone (LH) from the pituitary gland. These hormones stimulate production of ovarian sex steroids and continuous exposure of the pituitary gland to GnRH agonists results in down-regulation of GnRH receptors and subsequent inhibition of the hypothalamic pituitary gonadal (HPG) axis, suppressing release of estrogen by the ovaries. Suppression of estrogen through sustained release of a GnRH agonist, administered concurrently with breast cancer therapeutic treatments, including, but not limited to, endocrine therapies, may be beneficial in the treatment of premenopausal and perimenopausal HR-positive breast cancer patients.

The leuprolide acetate injectable, 3-month extended release composition of the present disclosure for suppression of estrogen to postmenopausal levels in premenopausal and perimenopausal women with HR-positive breast cancer will provide another important option to include in the treatment regimen for HR-positive breast cancer patients.

This disclosure provides methods of suppressing ovarian function in subjects with HR-positive breast cancer by administering a therapeutically effective amount of a flowable, extended release composition of the invention comprising leuprolide. This disclosure also provides methods of treating HR-positive breast cancer in a subject by administering a therapeutic treatment for HR-positive breast cancer, concurrently with a flowable, extended release composition of the present invention. In these methods, the breast cancer may be advanced breast cancer. In these methods, the breast cancer may be metastatic or locally advanced. The breast cancer may be estrogen receptor (ER)-positive and/or progesterone receptor (PgR)-positive breast cancer. In these methods, the breast cancer may be HR-positive, human epidermal growth factor receptor 2 (HER2)-negative cancer.

In these methods, the subject may have a confirmed diagnosis of Stage I, II, III, or IV HR-positive breast cancer, such as HR-positive, HER2-negative breast cancer. The subject or patient may be a premenopausal or perimenopausal woman with HR-positive breast cancer. In these methods, the subject is a candidate for endocrine therapy with ovarian suppression. In these methods, the subject's last menstrual period may have been within 12 months prior to treatment with the leuprolide compositions of this disclosure. In these methods, prior to treatment with the leuprolide compositions of this disclosure, the subject may have had a baseline estradiol (E2) concentration of greater than 30 pg/mL and/or follicle stimulating hormone (FSH) concentration greater than 40 IU/L. In some embodiments, the subject may be a male with HR-positive breast cancer. In these methods, the subject may be at least 18 years of age. In these methods, the subject may at least 18 years of age and less than 40 years of age, or at least 18 years of age and less than 45 years of age, or at least 18 years of age and less than 55 years of age.

The methods of this disclosure may be used within a combined regimen for the treatment of HR-positive breast cancer by administering a flowable, extended release leuprolide composition subcutaneously, concurrently with a therapeutic treatment for HR-positive breast cancer. In these methods, the flowable, extended release composition may be administered to the subject about once every 90 days (i.e., once about every 3 months), for at least 2 doses, for at least 3 doses, for at least 4 doses, for at least 5 doses, for at least 6 doses, for at least 7 doses, for at least 8 doses, for at least 9 doses, for at least 10 doses, for at least 11 doses, for at least 12doses, for at least 13 doses, for at least 14 doses, for at least 15 doses, for at least 16 doses, for at least 17 doses, for at least 18 doses, for at least 19 doses, for at least 20 doses, or for additional doses, until clinical progressive disease, or unmanageable toxicity, is observed. Longer treatment periods, including more treatment cycles, are contemplated.

The methods of this disclosure may be used in the treatment of HR-positive breast cancer by administering a flowable, extended release leuprolide composition concurrently with one or more adjuvant endocrine therapies such as selective estrogen receptor modulators (SERMs), selective estrogen receptor degraders (SERDs), other drugs that decrease release of endogenous non-ovarian estrogen (e.g., aromatase inhibitors; AI). The methods of this disclosure may be used in the treatment of HR-positive breast cancer by administering a flowable, extended release leuprolide composition concurrently with one or more CDK4/6 inhibitors, PI3K inhibitors, and/or mTOR inhibitors.

In these methods, the flowable, extended release leuprolide composition may be administered concurrently with tamoxifen. Tamoxifen is a nonsteroidal SERM of the triphenylethylene based anti-oestrogen which exhibits anti-estrogenic effects in breast tissue by competitively binding to estrogen receptors in breast cells. Tamoxifen may be administered orally by tablet or solution, e.g., 20 mg once daily or 10 mg two times daily or as otherwise prescribed. In these methods, the flowable, extended release leuprolide composition may be administered concurrently with one or more of letrozole, anastrozole, and exemestane. Letrozole and anastrozole are non-steroidal aromatase inhibitors, which reduce estrogen levels by blocking the aromatase enzyme (also called estrogen synthase) responsible for producing estrogens through aromatization of androgens in adipose tissue. Letrozole may be administered orally by tablet, e.g., 2.5 mg tablet taken orally once daily or as otherwise prescribed. Anastrozole may also be administered orally by tablet, e.g., one 1 mg tablet taken orally once daily or as otherwise prescribed. Exemestane is a steroidal aromatase inhibitor may be administered orally by tablet, c.g., one 25 mg tablet taken orally once daily or as otherwise prescribed.

The methods of this disclosure may be used in the treatment of HR-positive breast cancer by administering a flowable, extended release composition comprising leuprolide concurrently with chemotherapy, such as anthracycline-based chemotherapy, or carboplatin-based chemotherapy. Anthracycline-based chemotherapy for breast cancer may include 5-FU, epirubicin, and cyclophosphamide (FEC). Carboplatin-based chemotherapy may include taxane (e.g., Docetaxel), Carboplatin in addition to Trastuzumab (e.g., TCH regimen). The HR-positive breast cancer therapy contemplated herein may include neoadjuvant and adjuvant therapy.

The therapeutic methods of this disclosure may result in suppression of the subject's estradiol (E2) production to postmenopausal levels (<20 pg/mL). The therapeutic methods of this disclosure may result in suppression of the subject's estradiol (E2) level to less than about 20 pg/mL by about 6 weeks or longer after administration of the leuprolide composition. In some instances, the method results in suppression the subject's estradiol level to less than about 20 pg/mL by about 12 weeks or longer after administration of the leuprolide composition, by about 24 weeks or longer after administration of the leuprolide composition, by about 36 weeks or longer after administration of the leuprolide composition, or by about 48 weeks or longer after administration of the leuprolide composition. In some instances, the method results in suppression of the subject's estradiol to less than about 20 pg/mL in more than about 80%, more than about 85%, more than about 90%, more than about 95%, or about 100%, or any whole number percent to any other whole number percent between 80% and 100%, of patients treated with the leuprolide composition. These results may be obtained by administration of the extended release leuprolide composition alone, or concurrently with tamoxifen or other anti-hormonal agents, aromatase inhibitors, CDK4/6 inhibitors, PI3K inhibitors, and/or mTOR inhibitors.

The therapeutic methods of this disclosure may result in suppression of the subject's estradiol (E2) level to less than about 10 pg/mL. The therapeutic methods of this disclosure may result in suppression of the subject's estradiol (E2) level to less than about 10 pg/mL by about 6 weeks or longer after administration of the leuprolide composition. In some instances, the method results in suppression the subject's estradiol level to less than about 10 pg/mL by about 12 weeks or longer after administration of the leuprolide composition, by about 24 weeks or longer after administration of the leuprolide composition, by about 36 weeks or longer after administration of the leuprolide composition, or by about 48 weeks or longer after administration of the leuprolide composition. In some instances, the method results in suppression of the subject's estradiol to less than about 10 pg/mL in more than about 80%, more than about 85%, more than about 90%, more than about 95%, or about 100%, or any whole number percent to any other whole number percent between 80% and 100%, of patients treated with the leuprolide composition. These results may be obtained by administration of the extended release leuprolide composition alone, or concurrently with tamoxifen or other anti-hormonal agents, aromatase inhibitors, CDK4/6 inhibitors, PI3K inhibitors, and/or mTOR inhibitors.

The therapeutic methods of this disclosure may result in suppression of the subject's estradiol (E2) level to less than about 2.7 pg/mL when the methods include administration of an aromatase inhibitor or similar therapeutic agent. In some instances, the method results in suppression the subject's estradiol level to less than about 2.7 pg/mL by about 6 weeks or longer after administration of the leuprolide composition administered concurrently with another therapy such as an aromatase inhibitor. In some instances, the method results in suppression the subject's estradiol level to less than about 2.7 pg/mL by about 12 weeks or longer after administration of the leuprolide composition administered concurrently with another therapy such as an aromatase inhibitor, by about 24 weeks or longer after administration of the leuprolide composition administered concurrently with another therapy such as an aromatase inhibitor, by about 36 weeks or longer after administration of the leuprolide composition administered concurrently with another therapy such as an aromatase inhibitor, or by about 48 weeks or longer after administration of the leuprolide composition administered concurrently with another therapy such as an aromatase inhibitor. In some instances, the method results in suppression of the subject's estradiol to less than about 2.7 pg/mL in more than about 80%, more than about 85%, more than about 90%, more than about 95%, or about 100%, or any whole number percent to any other whole number percent between 80% and 100%, of patients treated with the lcuprolide composition administered concurrently with another therapy such as an aromatase inhibitor. These results may be obtained by administration of the extended release leuprolide composition concurrently with letrozole, anastrozole, exemestane, and/or other aromatase inhibitors, anti-hormonal agents, CDK4/6 inhibitors, PI3K inhibitors, and/or mTOR inhibitors. These results may be obtained by administration of the extended release leuprolide composition concurrently with one or more of letrozole, anastrozole, and exemestane.

The therapeutic methods of this disclosure may result in suppression of the subject's follicle stimulating hormone (FSH) level to less than about 40 IU/L. In some instances, the method results in suppression the subject's FSH level to less than about 40 IU/L by about 6 weeks or longer after administration of the leuprolide composition. In some instances, the method results in suppression the subject's FSH level to less than about 40 IU/L by about 12 weeks or longer after administration of the leuprolide composition, by about 24 weeks or longer after administration of the leuprolide composition, by about 36 weeks or longer after administration of the leuprolide composition, or by about 48 weeks or longer after administration of the leuprolide composition. In some instances, the method results in suppression of the subject's FSH level to less than about 40 IU/L in more than about 80%, more than about 85%, more than about 90%, more than about 95%, or about 100%, or any whole number percent to any other whole number percent between 80% and 100%, of patients treated with the leuprolide composition. These results may be obtained by administration of the extended release leuprolide composition alone, or concurrently with tamoxifen or other anti-hormonal agents, aromatase inhibitors, CDK4/6 inhibitors, PI3K inhibitors, and/or mTOR inhibitors.

The therapeutic methods of this disclosure may result in suppression of the subject's menstruation cycle. In some instances, the method results in the absence of menses at about 6weeks or longer after administration of the leuprolide composition. In some instances, the method results in absence of menses by about 12 weeks or longer after administration of the leuprolide composition, by about 24 weeks or longer after administration of the leuprolide composition, by about 36 weeks or longer after administration of the leuprolide composition, or by about 48 weeks or longer after administration of the leuprolide composition. In some instances, the method results in absence of menses in more than about 80%, more than about 85%, more than about 90%, more than about 95%, or about 100%, or any whole number percent to any other whole number percent between 80% and 100%, of patients treated with the leuprolide composition. These results may be obtained by administration of the extended release leuprolide composition alone, or concurrently with tamoxifen or other anti-hormonal agents, aromatase inhibitors, CDK4/6 inhibitors, PI3K inhibitors, and/or mTOR inhibitors.

In exemplary embodiments of the treatment methods of this disclosure, about 28 mg of leuprolide free base equivalent (e.g., about 30 mg of leuprolide acetate), in a volume of about 0.375 mL of the flowable, extended release compositions of this disclosure, is administered subcutaneously to the HR-positive breast cancer patient. The maintenance doses of the same composition and amount of leuprolide acetate are preferably administered for at least 1 dose, at least 2 doses, for at least 3 doses, for at least 4 doses, for at least 5 doses, for at least 6 doses, for at least 7 doses, for at least 8 doses, for at least 9 doses, for at least 10 doses, for at least 11doses, for at least 12 doses, for at least 13 doses, for at least 14 doses, for at least 15 doses, for at least 16 doses, for at least 17 doses, for at least 18 doses, for at least 19 doses, for at least 20doses, or for additional doses, until clinical progressive disease, or unmanageable toxicity, is observed. Longer treatment periods, including more treatment cycles, are contemplated.

Dosages, schedules, and methods for the administration of leuprolide acetate compositions of this disclosure used to treat HR-positive breast cancer are disclosed in the examples below, but other dosages, schedules, and methods are contemplated.

All publications, patents, and patent documents are incorporated by reference herein, as though individually incorporated by reference. The invention will now be illustrated with the following non-limiting examples.

EXAMPLES

Example 1

Pharmacokinetic Simulations

Pharmacokinetic simulations were prepared to elucidate serum leuprolide concentrations and pharmacokinetic (PK) parameter estimates following administration of 30 mg of leuprolide acetate for injection every three months for two doses.

The simulations were performed using serum leuprolide concentration data taken from male subjects with advanced prostate cancer administered [ELIGARD® ((leuprolide acetate) for injectable suspension), 22.5 mg every 3 month (7.5 mg/month)]. Pharmacokinetic behavior of leuprolide following two, 30 mg leuprolide acetate injections, of a 3-month formulation (achieving 10 mg/month) was predicted. The simulations were performed using Phoenix WinNonlin software (v 6.4; Certara Corporation, Princeton, NJ).

Figure 2:
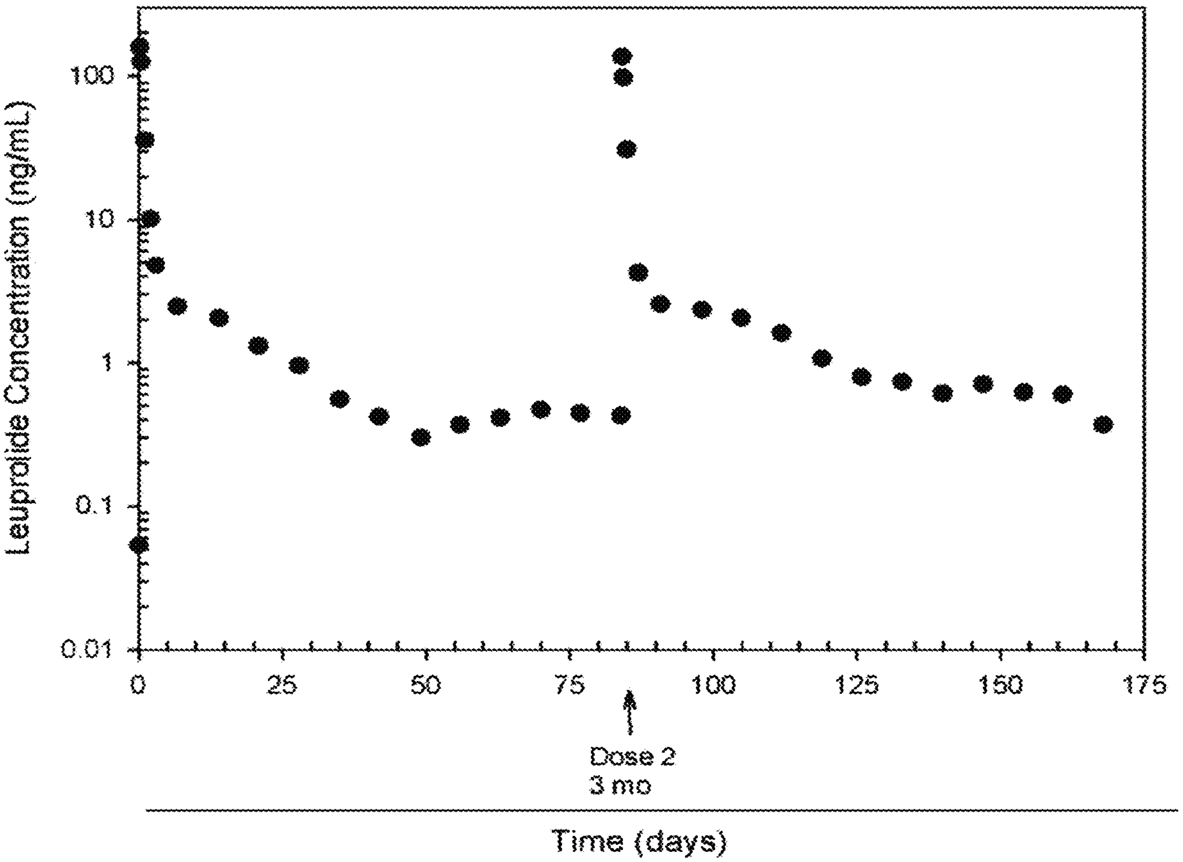
FIG. 2 shows log-linear serum leuprolide concentration-time profiles simulated for administration of 30 mg of leuprolide acetate injection every 3 months for 2 doses.
Figure 3:
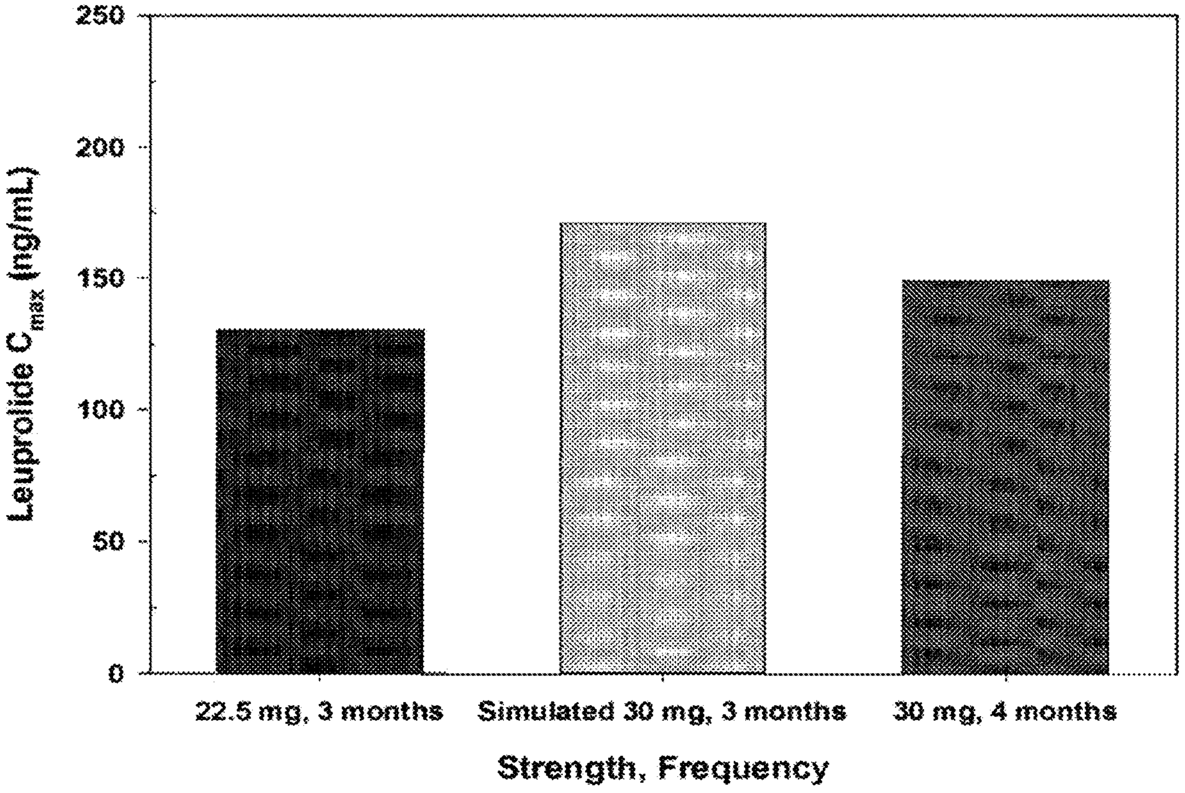
FIG. 3 shows the maximum plasma concentration (Cmax) simulated for administration of two amounts of leuprolide acetate in biodegradable polymers that release the leuprolide over 3 or 4 months.

Simulated plasma leuprolide concentration-time curves are presented in FIG. 1 (linear) and FIG. 2 (log-linear). PK parameters were estimated assuming dosing over 2 dosing intervals (once every 3 months), including burst kinetics following each dose (Table 1). PK parameters were also estimated without the 2 bursts (one after each dose; Table 2). $C_{max}$ was calculated for different doses of leuprolide acetate and different timed controlled release profiles of release of the drug from the 75:25 PLG biodegradable polymeric composition (FIG. 3).

TABLE 1

Simulated PK Parameter Estimates for Leuprolide Acetate Injection 30 mg Administered Subcutaneously Once Every 3 Months for 2 Doses: All Simulated Data

| Statistic | $T_{max}$ (day) | $C_{max}$ (ng/mL) | $AUC_{0\text{-}84\ days}$ (day · ng/mL) | $AUC_{84\text{-}168\ days}$ (day · ng/mL) | $AUC_{0\text{-}168\ days}$ (day · ng/mL) | $AUC_\tau$ (day · ng/mL) | $C_{avg}$ (ng/mL) | $C_{last}$ (ng/mL) |
|---|---|---|---|---|---|---|---|---|
| N | 23 | 23 | 23 | 23 | 23 | 23 | 23 | 23 |
| Mean | 0.196 | 171.443 | 208.659 | 206.577 | 415.236 | 208.659 | 2.484 | 0.392 |
| SD | 0.064 | 52.148 | 64.911 | 62.666 | 107.528 | 64.911 | 0.773 | 0.24 |
| CV % | 32.8 | 30.4 | 31.1 | 30.3 | 25.9 | 31.1 | 31.1 | 61.3 |
| Min | 0.17 | 68.63 | 92.67 | 36.64 | 228.66 | 92.67 | 1.1 | 0.15 |
| Median | 0.17 | 171.57 | 204.47 | 198.93 | 382.88 | 204.47 | 2.43 | 0.34 |
| Max | 0.33 | 284.62 | 368.14 | 298.26 | 636.72 | 368.14 | 4.38 | 1.23 |

N—number of values;
SD—standard deviation;
CV %—percent coefficient of variation;
Min—minimum;
Max—maximum;
$C_{max}$—maximum observed plasma concentration;
$T_{max}$—time of $C_{max}$;
$AUC_{x\text{-}y\ days}$—simulated area under the concentration-time curve over a dosing interval;
$AUC_\tau$—area under the concentration-time curve at steady-state;
$C_{avg}$—average plasma concentration at steady-state;
$C_{last}$—last observed plasma concentration at steady-state.

TABLE 2

Simulated PK Parameter Estimates for Leuprolide Acetate Injection 30 mg Administered Subcutaneously Once Every 3 Months for 2 Doses: Without Post-dose Plasma Concentration Burst (after Each Injection) Simulated data without burst concentrations

| Statistic | $T_{max}$ (day) | $C_{max}$ (ng/mL) | $AUC_{3\text{-}84\ days}$ (day · ng/mL) | $AUC_{87\text{-}168\ days}$ (day · ng/mL) | $AUC_\tau$ (day · ng/mL) | $C_{avg}$ (ng/mL) | $C_{last}$ (ng/mL) |
|---|---|---|---|---|---|---|---|
| N | 23 | 23 | 23 | 23 | 23 | 23 | 23 |
| Mean | 4.739 | 5.184 | 79.12 | 98.591 | 86.196 | 1.026 | 0.392 |
| SD | 5.61 | 2.179 | 39.302 | 44.362 | 39.226 | 0.467 | 0.24 |
| CV % | 118.4 | 42 | 49.7 | 45 | 45.5 | 45.5 | 61.3 |
| Min | 3 | 2.57 | 10.12 | 34.95 | 14.84 | 0.18 | 0.15 |
| Median | 3 | 4.91 | 63.08 | 87.23 | 70.48 | 0.84 | 0.34 |
| Max | 28 | 11.31 | 188.37 | 223.35 | 192.25 | 2.29 | 1.23 |

N—number of values;
SD—standard deviation;
CV %—percent coefficient of variation;
Min—minimum;
Max—maximum;
$C_{max}$—maximum observed plasma concentration;
$T_{max}$—time of $C_{max}$;
$AUC_{x\text{-}y\ days}$—simulated area under the concentration-time curve over a dosing interval;
$AUC_\tau$—area under the concentration-time curve at steady-state;
$C_{avg}$—average plasma concentration at steady-state;
$C_{last}$—last observed plasma concentration at steady-state.

Example 2

Human Clinical Studies

A clinical study is conducted in human patients to evaluate ovarian suppression following subcutaneous administration of leuprolide acetate in breast cancer patients.

The primary objective of this clinical study is to assess suppression of estradiol to postmenopausal levels following administration of a leuprolide acetate polymeric formulation of this disclosure in greater than 85% of premenopausal human female subjects with hormone receptor-positive (HR-positive), human epidermal growth factor receptor 2 (HER2)-negative breast cancer.

The secondary objectives of the study are to assess the safety and tolerability of the a leuprolide acetate polymeric formulation in premenopausal subjects with HR-positive, HER2-negative breast cancer, and determine the pharmacokinetic profile of a leuprolide acetate polymeric formulation and the pharmacodynamic (PD) profile after a leuprolide acetate polymeric formulation administration in premenopausal subjects with HR-positive, HER2-negative breast cancer.

The study is conducted as a phase 3, single arm, open-label study evaluating the effectiveness of an injectable, extended-release depot formulation of 30 mg of leuprolide acetate suspension designed to release leuprolide acetate at a rate of 10 mg/month (the "leuprolide study formulation"), with a dosing period of 3 months, to suppress ovarian function in premenopausal women with HR-positive, HER2-negative early breast cancer.

The leuprolide study formulation is a suspension of leuprolide acetate 30 mg for subcutaneous (SC) injection, provided in a single-use kit. The kit consists of a 2-syringe mixing system, a sterile needle (18 gauge, ⅝-inch), a silica gel desiccant pouch to control moisture uptake. Each syringe is individually packaged. One syringe contains the polymeric delivery system and the other contains the lyophilized leuprolide acetate powder. When constituted, the leuprolide acetate is administered as a single dose with an injection volume of 0.5 mL, or less. The polymeric delivery system consists of poly-(DL-lactide-co-glycolide [PLG]) or poly (DL lactide-co-glycolide)-COO (PLGH) dissolved in N-methyl-2-pyrrolidone (NMP). The PLG co-polymer has a DL-lactide to glycolide molar ratio of 75:25. The PLG to NMP ratio is 45:55 (% weight/weight). The polymer solution is terminally sterilized by gamma irradiation. The final composition of the reconstituted product is provided in the following Table.

| Component | Amount |
|---|---|
| Leuprolide Acetate Delivered | 30.0 mg[a] |
| PLG Delivered | 158.6 mg |
| NMP Delivered | 193.9 mg |
| Injection Volume[b] | 0.375 mL |
| Total Delivered Amount[b] | 382.5 mg |

Abbreviations:
LA = leuprolide acetate;
NMP = N-methyl-2-pyrrolidone;
PLG = poly-(DL-lactide-co-glycolide;
w/w = weight to weight.
[a]Results in approximately 28 mg leuprolide free base equivalent.
[b]Total injection volume and amount are theoretical and may be less as result of mixing and hold-up losses in the syringe and needle upon injection of the reconstituted product, based upon existing product label information.

The 2-syringe mixing system kit is brought to room temperature at least 30 minutes prior to reconstitution and administration. Once the contents of the 2 syringes are mixed, the final product is administered in less than 30 minutes.

The human subjects participate in the study for up to 56 weeks, including a screening period of up to 4 weeks, a treatment period of 48 weeks, and an end of study visit within 4 weeks of the final treatment period visit. Eligible subjects enter into the treatment period in 1 of 2 groups: those who are to receive tamoxifen concurrently with the leuprolide study formulation or those who are to initiate therapy with an aromatase inhibitor (AI) (letrozole, anastrozole, or exemestane) beginning 6 weeks after the first administration of the leuprolide study formulation. The study design schematic is presented in FIG. 4.

Figure 4:
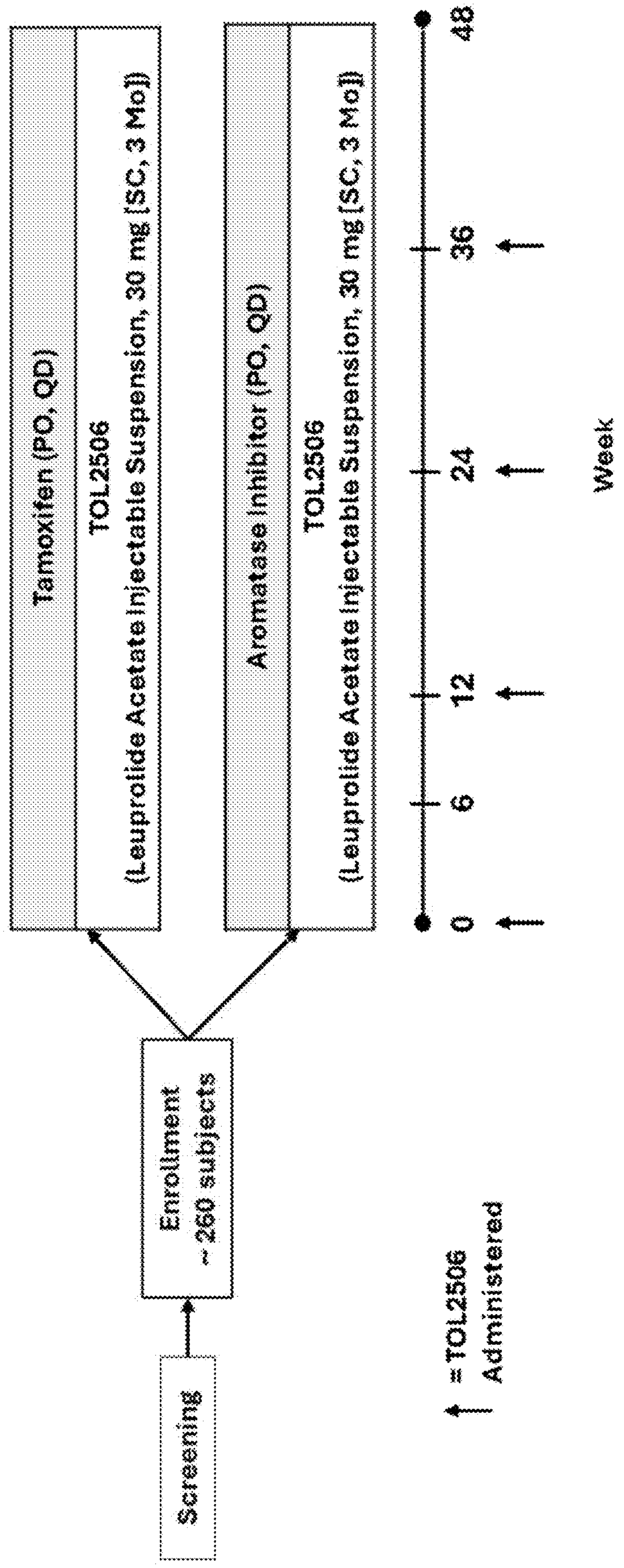
FIG. 4 shows a schematic representation of a human clinical study of the efficacy of an injectable, extended-release depot formulation of 30 mg of leuprolide acetate suspension designed to release leuprolide acetate at a rate of 10 mg/month over 3 months ("TOL2506"). The arrows indicate administrations of a dose of TOL2506. (Abbreviations: mo=month; QD=daily; SC=subcutaneous; PO=administered orally.)

At the time points indicated in FIG. 4, the leuprolide study formulation is administered as a subcutaneous injection given 84±2 days apart (i.e., every 12 weeks) for 48 weeks. Tamoxifen, or AI therapy is administered as a daily oral dose according to product labeling for these commercially available drugs. At the end of the treatment period, subjects are eligible for continued treatment on a compassionate use (expanded access) basis.

Approximately 260 subjects are enrolled in the study, and all qualified subjects receive the leuprolide study formulation. The principal investigator conducting the study, in consultation with the subject, determines whether the subject will receive tamoxifen beginning concurrently with the leuprolide study formulation, or treatment with letrozole, anastrozole or exemestane beginning 6 weeks after the first administration of the leuprolide study formulation/mL. No dose adjustment is allowed for the leuprolide study formulation. Dose adjustments of tamoxifen, letrozole, anastrozole, and exemestane and/or switching between tamoxifen and AI are made at the discretion of the investigator.

As appropriate, a subject is prematurely discontinued from the study, and efforts are made to collect all clinical and laboratory data as scheduled for the end of treatment visit and the subject followed up for safety, and the investigator completes and reports, as thoroughly as possible, the reasons for subject withdrawal.

Subjects enrolled meet all the following inclusion criteria:

1. Able to understand the investigational nature of this study and provide written informed consent prior to the participation in the trial.
2. Premenopausal female between 18 and 55 years of age, inclusive.
3. Have a confirmed diagnosis of Stage I, II, III, IV HR-positive, HER2-negative breast cancer.
4. Is a candidate for endocrine therapy+ovarian suppression.
5. Premenopausal status is defined as either:
   a. Baseline E2 of >30 pg/mL;
   b. Last menstrual period was within the last 12 months; and/or
   c. In case of therapy induced amenorrhea, plasma estradiol must be >30 pg/mL and/or FSH must be >40 IU/mL.

The subjects enrolled do not meet any the following exclusion criteria:

1. Have a body mass index (BMI) <15.00 $kg/m^2$.
2. Breastfeeding female.
3. Life expectancy <12 months.
4. Active or ongoing non-breast malignancy.
5. Have an Eastern Cooperative Oncology Group (ECOG) performance status ≥3.
6. Prior tamoxifen, other selective estrogen-receptor modulators (e.g., raloxifene) or antagonists (e.g., fulvestrant), aromatase inhibitor/in-activators, mTOR inhibitors, or hormone replacement therapy within 1 year before breast cancer diagnosis.
7. Prior neoadjuvant or adjuvant endocrine therapy since diagnosis of breast cancer.
8. Any other medical condition or serious intercurrent illness or the presence of clinically significant findings on the physical exam, laboratory testing, medical history, that in the opinion of the Investigator may interfere with trial conduct, subject safety, or interpretation of study results.
9. Subject who is already receiving and/or previously received GnRH analogs within 1 year before breast cancer diagnosis.
10. Psychiatric, addictive, or other disorders that would preclude study compliance.
11. Use of any recreational drugs (cocaine, amphetamines, barbiturates, benzodiazepines, and morphine) or history of drug or alcohol abuse within the past 6 months, or a positive result on the urine drug/alcohol screen (a single re-test may be administered within 2 weeks of the initial result).
12. Medications that are liable to impact subject safety and/or affect the PK of the drug and hormonal assessments including but not limited to:
    a. Oral or transdermal hormonal therapy within 30 days prior to screening;
    b. Estrogen, progesterone, or androgens within 30 days prior to screening; and/or
    c. Hormonal contraceptives within 30 days prior to screening.

13. Known hypersensitivity, idiosyncratic, or allergic reactions to GnRH, GnRH agonist analogs or to any of the components of the IP.
14. Female subjects who are sexually active with a male partner and not willing to use non hormonal contraceptive methods throughout the study.
15. Women of childbearing potential with a positive serum pregnancy test at Screening and/or Day 0.
16. Unacceptable hematology status:
    a. Hemoglobin≤9 g/dL;
    b. Absolute neutrophil count≤1500 cells/μL; and/or
    c. Platelet count≤75,000 cells/μL.
17. Unacceptable liver function:
    a. Alanine aminotransferase (ALT)≥2× upper limit of normal (ULN);
    b. Aspartate aminotransferase (AST)≥2× ULN;
    c. Bilirubin≥2× ULN; and/or
    d. Alkaline phosphatase≤2× ULN.
18. Unacceptable kidney function:
    a. Creatinine≥3× ULN; and/or
    b. Creatinine clearance≤30 mL/minute.
19. Exposure to any investigational agent within 60 days prior to first dose of the leuprolide study formulation, at the discretion of the Investigator and the Sponsor/DSMB.
20. Donation and/or loss of blood (1 unit or 350 ml) within 90 days prior to receiving the first dose of the leuprolide study formulation.

Subjects are discontinued from the study for any of the following reasons:

1. Subject withdrawal of consent.
2. Discretion of investigator.
3. Subject becomes pregnant.
4. Changes in the subject's condition that, in the judgment of the investigator, render the subject unacceptable for further treatment with the study drug.
5. Serious adverse event(s) (AE(s)) or AE(s) that, in the judgment of the investigator, render the subject unacceptable for further study drug treatment.
6. Subject noncompliance with the study protocol.
7. Termination of the study by the Sponsor, Institutional Review Board (IRB) or Independent Ethics Committee (IEC), or other regulatory authorities.
8. Subject fails suppression of estradiol to postmenopausal levels (<20 pg/mL) at 2consecutive visits after Week 6.

This study is an open label study, and all enrolled subjects receive the leuprolide study formulation. The investigator, in consultation with the subject, decides whether the subject receives concomitant treatment with tamoxifen, letrozole, anastrozole, or exemestane. The study is not stratified for tamoxifen or letrozole/anastrozole/exemestane treatment. Those patients receiving tamoxifen receive tamoxifen administered orally by tablet or solution, 20 mg once daily or 10 mg twice daily. Those patients receiving aromatase inhibitors, receive either letrozole at one 2.5 mg tablet taken orally once daily; or anastrozole at one 1 mg tablet taken orally once daily; or exemestane at one 25 mg tablet taken orally once daily.

The leuprolide study formulation is administered as a subcutaneous injection. The specific location chosen for injection of the leuprolide study formulation is an area with sufficient soft or loose subcutaneous tissue (e.g., upper- or mid-abdominal areas). Areas with brawny or fibrous subcutaneous tissue or locations that could be rubbed or compressed (e.g., with a belt or clothing waistband) are avoided. Topical or local anesthetic to "numb" the study drug injection site is permitted but is recorded as a concomitant medication including the time of its administration.

In the screening period, subjects sign informed consent and are screened on the basis of demographics, physical examination including vital signs, ECOG status, past medical/surgical history, medication history, electrocardiogram (ECG), and laboratory investigations (including baseline estrone [E1], estradiol, FSH, and LH). Menses status is collected at screening and at each visit. BMI is recorded at screening and at each dosing visit.

Eligible subjects enter into the Treatment Period in 1 of 2 groups: those who are to receive tamoxifen concurrently with the leuprolide study formulation or those who are to initiate therapy with letrozole, anastrozole, or exemestane beginning 6 weeks after the first administration of the leuprolide study formulation as determined by the investigator. Both groups receive the first administration of the leuprolide study formulation on Day 0. The subsequent 3 doses of the leuprolide study formulation are administrated on Days 84 (Week 12), 168 (Week 24), and 252 (Week 36). A window of +3 days is allowed for the administration of the leuprolide study formulation. Study subjects report to the clinical site for IP administration on these days and assessments through 8 hours post dose.

Additional subject visits occur on Weeks 2, 4, and 6. Blood samples for PK and PD assessments are collected at Baseline (Day 0), Week 6, 12, 24, 36, and 48 in all subjects. Samples collected on a dosing visit are collected 30 minutes prior to the leuprolide study formulation administration. On dosing visits occurring at Week 0 and Week 12, the pre-dose blood sample is followed by samples collected 4 hours and 8 hours after administration.

For a subset of 20 subjects, additional visits within the first 24 weeks are necessary for PK samples to be collected. Estradiol from samples collected at Weeks 2, 4, 6, 12, 24, 36,and 48 is measured by a high sensitivity validated liquid chromatography-tandem mass spectrometric method. Fifteen blood samples of 3 mL each for measurement of El, estradiol, FSH, LH, and progesterone are collected in tubes containing K2EDTA anticoagulant at pre-specified time points. Hormone analyses methods are outlined in the following table:

Hormone Analyses

| Hormone (Units) | Analytical Method | Lower Limit of Quantitation |
|---|---|---|
| E1 (pg/mL) | Unconjugated estrone LC/MS/MS | 2.5 |
| E2 (pg/mL) | LC/MS/MS | 1 |
| FSH (mIU/mL) | ELISA | 1 |
| LH (mIU/mL) | ELISA | 1 |
| Progesterone (pg/mL) | LC/MS/MS | 20 |

Abbreviations:
E1 = estrone;
E2 = estradiol;
ELISA = enzyme-linked immunosorbent assay;
FSH = follicle stimulating hormone;
LC = liquid chromatography;
LH = luteinizing hormone;
MS = mass spectrometry.

After completion of the treatment period, subjects are eligible to continue treatment with the leuprolide study formulation through compassionate use (expanded access) for up to 4 additional years.

Steady-state and/or pre-dose concentrations of leuprolide levels are the statistical description of the leuprolide concentrations collected at each assessment point at least 1 month after the first administration and prior to subsequent administration of the leuprolide study formulation. The area under the concentration curve over the dosing interval at steady state (area under the curve, $AUC_{tau\ ss}$) of the systemic leuprolide concentration between each dose and for the entire treatment period is provided. Maximum serum leuprolide concentrations (maximum concentration [$C_{max}$] or maximum concentration at steady state [$C_{max\ ss}$]) as well as time to $C_{max}$ and time to $C_{max}$ ss ($T_{max}$ and $T_{max\ ss}$, respectively) is determined during each dosing interval. Steady-state average concentration and, time to steady-state is estimated from predose (concentration immediately prior to dose administration) concentrations.

Subjects are monitored throughout study participation for occurrence of AEs as well as for changes in vital signs, and laboratory data. Gynecological exams can be performed per investigator discretion when medically indicated.

Blood glucose level, glycosylated hemoglobin, and electrolytes and bone density may be measured at screening, periodically during the course of the trial, and at the End of Study Visit.

Data on disease classification (histological type and stage of carcinoma) and diagnostic imaging/extent of disease are collected for all study subjects, and the TNM classification system will be used to grade the extent of the disease. Complete demographic and medical history information is obtained during the initial screening visit, and all concurrent medical conditions in the last 60 days and any significant medical conditions (e.g., hospitalizations, surgeries, prior cancer history, etc.) are collected. Thereafter, any information and report of an untoward event is collected as an adverse event (AE). An AE is the development of an undesirable medical condition or the deterioration of a preexisting medical condition following enrollment in a clinical study, including but not limited to following or during exposure to a pharmaceutical product, whether or not considered casually related to the product. In clinical studies, an AE can include an undesirable medical condition occurring at any time, including baseline or washout periods, even if no study treatment has been administered. A Serious Adverse Event (SAE) is an AE that fulfils 1 or more of: results in death, is immediately life-threatening, requires in-subject hospitalization or prolongation of existing hospitalization, results in persistent or significant disability or incapacity, results in a congenital abnormality or birth defect, is an important medical event that may jeopardize the subject or may require medical intervention to prevent any one of these outcomes. An unexpected adverse reaction is any untoward and unintended response that is related to the administration of the leuprolide study formulation at any dose that is not consistent with the applicable product information.

All concomitant medications administered during each study subject's participation until the end of this study is recorded. Vital signs measurements taken and recorded from each study participant include systolic and diastolic blood pressure, heart rate, respiration or pulse rate, and temperature (blood pressure and heart rate are recorded after the subject has rested in the sitting position for at least 5 minutes). A physical examination (PE) is performed on all study subjects, including examination of skin, head, eyes, cars, nose, and throat, lymph nodes, heart, chest, lungs, abdomen, extremities, and neurologic, including height and weight. BMI is recorded at beginning and end of each dosing interval. A full PE is conducted at Screening. Subsequently, an abbreviated PE is conducted, although a full PE may be conducted at the discretion of the investigator.

A 12-lead ECG is obtained in triplicate and includes heart rate, PR interval, QRS duration, QT interval, and corrected QT (QTc) interval (the ECG measurements are made after the subject has rested in a supine position for at least 10 minutes before the assessment). Any ECG results outside the normal ranges are repeated at the discretion of the investigator. Any results outside the normal ranges deemed clinically significant are recorded as an adverse event. Bone density is measured using dual energy X-ray absorptiometry (DEXA) scans.

The hematology and clinical chemistry laboratory analyses is performed for each study participant at a local laboratory and includes complete blood cell count, white blood cell count, and urinalysis.

Evaluation of blood samples collected from study participants at the Week 6 visit shows that greater than 85% of the study subjects had estradiol levels less than 20 μg/mL, indicative of ovarian suppression.

Additional evaluation of blood samples collected from study participants treated with the leuprolide study formulation and tamoxifen shows that greater than 85% of those study subjects had estradiol levels less than 20 pg/mL at one or more of Weeks 12, 24, 36, and 48 of the study.

Additional evaluation of blood samples collected from study participants treated with the leuprolide study formulation and letrozole, anastrozole, or exemestane shows that greater than 85% of those study subjects had estradiol levels less than 2.7 pg/mL at one or more of Weeks 12, 24, 36, and 48 of the study.

Additional evaluation of blood samples collected from all study participants shows that greater than 85% of those study subjects had FSH levels less than 40 IU/L at one or more of Weeks 6, 12, 24, 36, and 48 of the study.

Additional evaluation of study participant data shows that the majority of participants report an absence of menses at one or more of Weeks 6, 12, 24, 36, and 48.

The percent change in baseline estradiol and FSH levels (from "baseline levels" collected from each study participant before the first dose of the leuprolide study formulation) is determined by analysis of study participant blood samples collected at Weeks 6, 12, 24, 36, and 48. Similarly, the number (percent) of study subjects with clinically significant suppressed mean serum LH levels at 6, 12, 24, 36, and 48 weeks (compared to baseline levels) is determined. Similarly, the number (percent) of study subjects with clinically significant suppressed mean serum FSH levels at 6, 12, 24, 36, and 48 weeks (compared to baseline levels) is determined. Similarly, the statistical change in serum E1 and progesterone levels of study subjects (compared to baseline levels) is determined at 6, 12, 24, 36, and 48 wecks.

The various features and processes described above may be used independently of one another or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising", "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. The accompanying claims and their equivalents are intended to cover such forms or modifications as would fall within the scope and spirit of certain of the inventions disclosed herein.

What is claimed is:

1. An extended release composition for use in suppressing ovarian function during treatment of hormone receptor-positive breast cancer in pre- or peri-menopausal women, comprising a biodegradable polymer comprising co-polymer segments of poly(lactide-co-glycolide) (PLG) having a lactide to glycolide molar ratio of 70:30 to 80:20, no titratable carboxylic acid groups, and at least one distal end that is hydroxyl-terminated;

N-methyl-2-pyrrolidone (NMP); and leuprolide or a pharmaceutically acceptable salt thereof, present in an amount to provide 26 mg to 30 mg of a free base equivalent of leuprolide;

wherein the extended release composition has an injection volume of less than 0.5mL;

wherein the extended release composition comprises 35-60% by weight of the biodegradable polymer and 50-60% by weight of NMP; and wherein the extended release composition is a 3-monthly formulation formulated to release up to 10 mg/mL leuprolide per month when administered subcutaneously every three months to pre-or peri-menopausal women with hormone receptor-positive breast cancer.

2. The extended release composition of claim 1, wherein the biodegradable polymer has a weight average molecular weight of from 15 kDa to 45 kDa.

3. The extended release composition of claim 1, wherein the biodegradable polymer has a weight average molecular weight of from 17 kDa to 21 kDa.

4. The extended release composition of claim 1, wherein the biodegradable polymer is 1,6-hexanediol-initiated.

5. The extended release composition of claim 1, wherein the biodegradable polymer has a lactide to glycolide molar ratio of 75:25.

6. The extended release composition of claim 1, wherein the biodegradable polymer has a formula HO—(P)—C(═O)O—Ra—O(O═)C—(P)—OH wherein Ra is an alkane diradical comprising 4 to 8 carbons and P is a polymeric segment comprising units of lactide, glycolide, or (lactide-co-glycolide).

7. The extended release composition of claim 1, wherein the extended release composition comprises from 28 mg to 32 mg of leuprolide acetate.

8. The extended release composition of claim 1, wherein the extended release composition comprises 30 mg of leuprolide acetate.

9. The extended release composition of claim 1, wherein the extended release composition has an injection volume of 0.375 mL.

10. A dual syringe system for use in suppressing ovarian function during treatment of hormone receptor-positive breast cancer in pre-or peri-menopausal women, comprising an extended release composition comprising a biodegradable polymer comprising co-polymer segments of poly(lactide-co-glycolide) (PLG) having a lactide to glycolide molar ratio of 70:30 to 80:20, no titratable carboxylic acid groups, and at least one distal end that is hydroxyl-terminated;

N-methyl-2-pyrrolidone (NMP); and leuprolide or a pharmaceutically acceptable salt thereof, present in an amount to provide 26 mg to 30 mg of a free base equivalent of leuprolide;

wherein a first syringe comprises the biodegradable polymer and NMP, and a second syringe comprises leuprolide or the pharmaceutically acceptable salt thereof;

wherein the extended release composition in the dual syringe system has an injection volume of less than 0.5 mL;

wherein the extended release composition comprises 35-60% by weight of the biodegradable polymer and 50-60% by weight of NMP; and wherein the extended release composition is a 3-monthly formulation formulated to release up to 10 mg/mL leuprolide per month when administered subcutaneously every three months to pre-or peri-menopausal women with hormone receptor-positive breast cancer.

11. The dual syringe system of claim 10, wherein the biodegradable polymer has a weight average molecular weight of from 15 kDa to 45 kDa.

12. The dual syringe system of claim 10, wherein the biodegradable polymer has a weight average molecular weight of from 17 kDa to 21 kDa.

13. The dual syringe system of claim 10, wherein the biodegradable polymer is 1,6-hexanediol-initiated.

14. The dual syringe system of claim 10, wherein the biodegradable polymer has a lactide to glycolide molar ratio of 75:25.

15. The dual syringe system of claim 10, wherein the biodegradable polymer has a formula HO—(P)—C(═O)O—Ra—O(O═)C—(P)—OH wherein Ra is an alkane diradical comprising 4 to 8 carbons and P is a polymeric segment comprising units of lactide, glycolide, or (lactide-co-glycolide).

16. The dual syringe system of claim 10, wherein the extended release composition comprises from 28 mg to 32 mg of leuprolide acetate.

17. The dual syringe system of claim 10, wherein the extended release composition comprises 30 mg of leuprolide acetate.

18. The dual syringe system of claim 10, wherein the extended release composition in the dual syringe system has an injection volume of 0.375 mL.

19. A kit comprising the dual syringe system of claim 10 and instructions for using the dual syringe system to administer the extended release composition by subcutaneous injection for suppression of ovarian function during treatment of hormone receptor-positive (HR+) breast cancer in pre-or peri-menopausal women.

20. The kit of claim 19, wherein the instructions for using include instructions for administration to a pre-or peri-menopausal woman with HR+ breast cancer.

21. The kit of claim 19, wherein the instructions for using include instructions for administration of the extended release composition every three months to a pre-or peri-menopausal woman with HR+ breast cancer.

22. The kit of claim 19, wherein the instructions for using include instructions for mixing the contents of the first and second syringe together to form a flowable composition for administration to a subject.

23. The kit of claim 19, wherein the instructions for using describe administration of the extended release composition concurrently with tamoxifen or an aromatase inhibitor.

24. The kit of claim 19, wherein upon contact of the extended release composition with a bodily fluid, the NMP dissipates and an in situ solid or semi-solid depot forms.

* * * * *